US010758603B2

(12) United States Patent
Lin et al.

(10) Patent No.: US 10,758,603 B2
(45) Date of Patent: Sep. 1, 2020

(54) **COMPOSITION FOR PREVENTING AND TREATING *MYCOPLASMA HYORHINIS* INFECTION, AND METHOD FOR PRODUCING SAID COMPOSITION**

(71) Applicant: AGRICULTURAL TECHNOLOGY RESEARCH INSTITUTE, Hsinchu, Taiwan (CN)

(72) Inventors: Jiunn-Horng Lin, Hsinchu (CN); Zeng-Weng Chen, Hsinchu (CN); Jyh-Perng Wang, Hsinchu (CN); Chiung-Wen Hsu, Hsinchu (CN); Weng-Zeng Huang, Hsinchu (CN); Ming-Wei Hsieh, Hsinchu (CN); Tzu-Ting Peng, Hsinchu (CN); Shih-Ling Hsuan, Hsinchu (CN)

(73) Assignee: Agricultural Technology Research Institute, HsinChu (TW)

( * ) Notice: Subject to any disclaimer, the term of this patent is extended or adjusted under 35 U.S.C. 154(b) by 0 days.

(21) Appl. No.: 16/320,515

(22) PCT Filed: Aug. 9, 2016

(86) PCT No.: PCT/CN2016/094104

§ 371 (c)(1),
(2) Date: Jan. 25, 2019

(87) PCT Pub. No.: WO2018/027526

PCT Pub. Date: Feb. 15, 2018

(65) Prior Publication Data

US 2020/0023048 A1 Jan. 23, 2020

(51) Int. Cl.

*A61K 39/02* (2006.01)
*A61P 31/04* (2006.01)
*C07K 14/30* (2006.01)
*A61K 39/00* (2006.01)

(52) U.S. Cl.

CPC .......... *A61K 39/0241* (2013.01); *A61P 31/04* (2018.01); *C07K 14/30* (2013.01); *A61K 2039/55505* (2013.01); *C07K 2319/21* (2013.01); *C07K 2319/35* (2013.01)

(58) Field of Classification Search

None

See application file for complete search history.

(56) References Cited

U.S. PATENT DOCUMENTS 7,381,414 B2 * 6/2008 Lin .................... A61K 39/0241 424/184.1

9,561,267 B2 2/2017 Lin et al.

FOREIGN PATENT DOCUMENTS

WO WO 2014/121433 A1 8/2014

OTHER PUBLICATIONS

Chen et al., "Characterization and application of monoclonal antibodies against *Mycoplasma hyorhinis* pyruvate dehydrogenase El complex subunit alpha," *Appl. Microbiol. Biotechnol.* 100: 3587-3597, 2016.

Feng et al., "The Progress of Prevention for Mycoplasma Pneumonia of Swine," *Progress in Modern Biomedicine* 8(11): 2143-2145, 4 pages , 2008 (Abstract in English).

Gomersall et al., "The *Mycoplasma hyorhinis* p37 Protein Rapidly Induces Genes in Fibroblasts Associated with Inflammation and Cancer," *PLoS ONE* 10(10):e0140753.doi:10.1371/journal.pone.0140753, 24 pages , 2015.

Lee et al., "Reduction of mycoplasmal lesions and clinical signs by vaccination against *Mycoplasma hyorhinis," Veterinary Immunology and Immunopathology* 196: 14-17, 2018.

Liu et al., "Mycoplasma hyopneumoniae DnaK Gene and ELISA Method," *Journal of Jingling Institute of Technology* 27(4): 79-84, 2011 (Abstract in English).

Martinson et al., "Efficacy of an inactivated *Mycoplasma hyorhinis* vaccine in pigs," *Vaccine* 36: 408-412, 2018.

Notarnicola et al., "A *Mycoplasma hyorhinis* protein with sequence similarities to nucleotide-binding enzymes," *Gene* 97: 77-85, 1991.

Rosengarten et al., "The Vlp System of *Mycoplasma hyorhinis*: Combinatorial Expression of Distinct Size Variant Lipoproteins Generating High-Frequency Surface Antigenic Variation," *Journal of Bacteriology* 173(15): 4782-4793, 1991.

Urbanek et al., "Detection of antibodies directed at *M. hyorhinis* p37 in the serum of men with newly diagnosed prostate cancer," *BMC Cancer* 11: 233, 6 pages, 2011.

Xiong et al., "Characterization of the role in adherence of *Mycoplasma hyorhinis* variable lipoproteins containing different repeat unit copy numbers," *Veterinary Microbiology* 197: 39-46, 2016.

Yogev et al., "Sequence and TnphoA Analysis of a *Mycoplasma hyorhinis* Protein with Membrane Export Function," *Journal of Bacteriology* 173(6): 2035-2044, 1991.

* cited by examiner

*Primary Examiner* — Brian Gangle

(74) *Attorney, Agent, or Firm* — Seed IP Law Group LLP

(57) ABSTRACT

Disclosed is a composition for preventing and treating a *Mycoplasma hyorhinis* infection in swine. The composition uses XylF, DnaK, P72, or a combination thereof as an active pharmaceutical ingredient. Further disclosed are an expression vector and a method for producing the active pharmaceutical ingredient of the composition using a prokaryotic expression system.

17 Claims, 1 Drawing Sheet

Specification includes a Sequence Listing.

COMPOSITION FOR PREVENTING AND TREATING *MYCOPLASMA HYORHINIS* INFECTION, AND METHOD FOR PRODUCING SAID COMPOSITION

BACKGROUND OF THE INVENTION

Statement Regarding Sequence Listing

The Sequence Listing associated with this application is provided in text format in lieu of a paper copy, and is hereby incorporated by reference into the specification. The name of the text file containing the Sequence Listing is 100224_401USPC_SEQUENCE_LISTING.txt. The text file is 54 KB, was created on Jan. 21, 2019, and is being submitted electronically via EFS-Web.

Field of the Invention

The present disclosure relates to a composition against *Mycoplasma hyorhinis* infection, especially to a subunit vaccine against *Mycoplasma hyorhinis* infection.

Description of the Prior Art

*Mycolplasma hyopneumoniae* and *Mycoplasma hyorhinis* are the main pathogens causing swine enzootic pneumonia, SEP. *Mycoplasma hyorhinis* is also involved in outbreak of polyserositis or arthritis. Infection by either *Mycolplasma hyopneumoniae* or *Mycoplasma hyorhinis*, will reduce feeding efficiency and cause growth retardation of swine as well as make swine more vulnerable to secondary infection of other viral or bacterial pathogens, which therefore leads to economic loss of pig farming industry. Inactivated (killed) *Mycolplasma hyopneumoniae* vaccines have been developed by the manufacturers of animal vaccines in the world and have been widely used in pig farming industry. However, no *Mycoplasma hyorhinis* vaccine has appeared on the market yet. Administration of inactivated *Mycolplasma hyopneumoniae* vaccines can merely prevent *Mycolplasma hyopneumoniae* infection, but can't protect pigs from *Mycoplasma hyorhinis* infection.

In order to resolve the problem of insufficient protection of the present vaccines, it is necessary to develop a *Mycoplasma hyorhinis* vaccine. The conventional vaccines in this field are mainly inactivated (killed) vaccines. As *Mycoplasma* spp. is not easy to be cultured, the culture medium for them is expensive and the concentration of *Mycoplasma* spp. acquired therefrom is not high enough, the manufacturing cost of inactivated (killed) *Mycoplasma hyorhinis* vaccines remains high. Therefore, a subunit vaccine which is easy to produce and has high safety is considered as another option in vaccine development. To date, the antigens suitable for use in *Mycoplasma hyorhinis* vaccines have not yet been proposed by any well-established research report in this field. In view of the above, the main object of the present disclosure is to develop a low-cost and effective *Mycoplasma hyorhinis* subunit vaccine, thereby improving overall epidemic prevention work in pig farming industry.

SUMMARY OF THE INVENTION

One object of the present disclosure is to provide a subunit vaccine against *Mycoplasma hyorhinis* infection, thereby improving epidemic prevention work in pig farming industry.

Another object of the present disclosure is to provide an antigen expression vector, and a method for producing a subunit vaccine wherein the antigen gene in said expression vector is expressed in a prokaryotic expression system, thereby reducing the production cost of said subunit vaccine.

In order to achieve said objects, the present disclosure provides a composition for avoiding the diseases caused by *Mycoplasma hyorhinis* infection, comprising an active ingredient comprising XylF, DnaK, P72 or a combination thereof, and an adjuvant; wherein said XylF comprises SEQ ID NO: 01, said DnaK comprises SEQ ID NO: 02, and said P72 comprises SEQ ID NO: 03; wherein said disease is at least one selected from peritonitis, pleurisy, pericarditis and joint swelling.

Preferably, said active ingredient comprises at least two selected from a group consisting of XylF, DnaK, P72 or a combination thereof; more preferably, said active ingredient comprises a combination of XylF, DnaK and P72.

Preferably, said active ingredient has a concentration of 50 to 300 μg/mL, based on the total volume of said composition.

Preferably, said adjuvant comprises complete Freund's adjuvant, incomplete Freund's adjuvant, alumina gel, surfactant, anionic polymer, peptide, oily emulsion, or a combination thereof.

Preferably, said disease is peritonitis, pleurisy or a combination thereof provided that said active ingredient is XylF.

Preferably, said disease is peritonitis provided that said active ingredient is DnaK.

Preferably, said disease is pleurisy provided that said active ingredient is P72.

Preferably, wherein said disease is peritonitis, pleurisy, pericarditis and joint swelling provided that said active ingredient is a combination of XylF, DnaK and P72.

Furthermore, the present disclosure provides an expression vector for production of the active ingredient of said composition in a prokaryotic expression system, wherein said expression vector comprises:

an expression element, comprising a promoter and a ribosome binding site;

a nucleotide sequence encoding said XylF, said DnaK, said P72, or a combination thereof; and a sequence encoding a fusion partner;

wherein said nucleotide sequence comprises SEQ ID NO: 04, SEQ ID NO: 05 or SEQ ID NO: 06, or a combination thereof.

Preferably, the fusion partner is DsbC of *E. coli*, MsyB of *E. coli*, FklB of *E. coli*, or a combination thereof. More preferably, for the expression vector, said fusion partner is DsbC of *E. coli* provided that said nucleotide sequence encodes XylF; said fusion partner is MsyB of *E. coli* provided that said nucleotide sequence encodes DnaK; or said fusion partner is FklB of *E. coli* provided that said nucleotide sequence encodes P72.

Preferably, said expression vector further comprises a sequence encoding histidine-tag (His-tag), glutathione S-transferase (GST-tag) or a combination thereof.

Preferably, said expression vector comprises SEQ ID NO: 07, SEQ ID NO: 08, or SEQ ID NO: 09.

Preferably, said prokaryotic expression system is *E. coli* expression system.

The present disclosure further provides a method for production of a soluble protein; wherein said protein is XylF, DnaK, P72, or a combination thereof; wherein said method comprising (1) providing a prokaryotic expression system; and (2) expressing said nucleotide sequence of the expression vector in said prokaryotic expression system.

Preferably, said method further comprising a step of passing the product obtained in the above step (2) through a nickel ion affinity column or a glutathione affinity column to obtain said soluble protein.

In summary, the present disclosure provides a composition against *Mycoplasma hyorhinis* infection, thereby the goal of avoiding the diseases caused by *Mycoplasma hyorhinis* infection can be achieved. The present disclosure also discloses an antigen expression vector and a method for production of said active ingredient of said composition in a prokaryotic expression system.

DETAILED DESCRIPTION OF THE EMBODIMENTS

Figure 1:
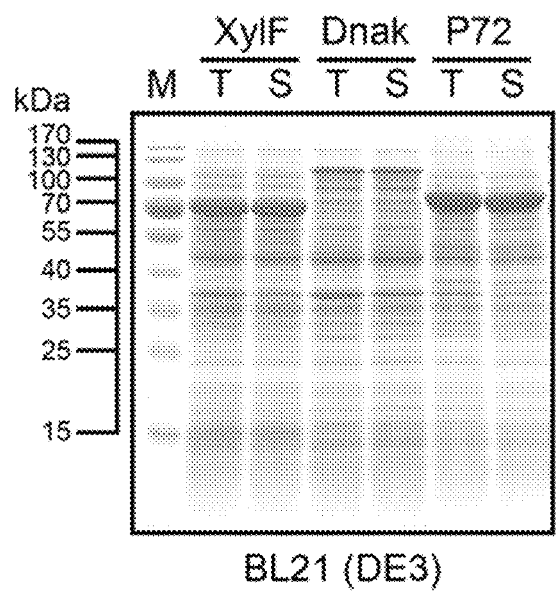
FIG. 1 shows the result of protein electrophoresis conducted in Example 3 for observing the solubility of the recombinant antigen of the present disclosure (wherein T represents total cell lysates and S represents the soluble fraction in total cell lysates.

In view of absence of compositions against *Mycoplasma hyorhinis* infection, the present inventor performed profound research and has proved that XylF, DnaK and P72, alone or in combination can be used as active ingredients of a composition for avoiding a disease caused by *Mycoplasma hyorhinis* infection. The term "a disease caused by *Mycoplasma hyorhinis* infection" in this text means at least one disease selected from peritonitis, pleurisy, pericarditis and joint swelling. In an embodiment, "said disease caused by *Mycoplasma hyorhinis* infection" can be evaluated by a method proposed by Magnusson et al. (Vet. Immunol. Immunopathol., 61:83-96, 1998).

In one example, the result of the experiment of the present disclosure showed that XylF, when used as an active ingredient of the composition of the present disclosure, is especially useful in alleviation of peritonitis, pleurisy or a combination thereof. In another example of the present disclosure, the result of the experiment showed that DnaK, when used as an active ingredient of the composition of the present disclosure, is especially useful in alleviation of peritonitis. In a further example of the present disclosure, the result of the experiment showed that P72, when used as an active ingredient of the composition of the present disclosure, is especially useful in alleviation of pleurisy. In a furthermore example of the present disclosure, the result of the experiment showed that a combination of XylF, DnaK and P72, when used as active ingredients, is especially useful provided that the diseases to be alleviated are peritonitis, pleurisy, pericarditis and joint swelling.

In one aspect, the present disclosure provides a composition for avoiding diseases caused by *Mycoplasma hyorhinis* infection. Said composition comprises an active ingredient and an adjuvant. The term "active ingredient" means an ingredient that can achieve the purpose of using said composition. Said active ingredient comprises XylF, DnaK, P72 or a combination thereof; wherein said XylF comprises SEQ ID NO: 01, said DnaK comprises SEQ ID NO: 02, and said P72 comprises SEQ ID NO: 03.

In an embodiment, said active ingredient is one selected from a group consisting of XylF, DnaK and P72. In another embodiment, said active ingredient comprises two selected from a group consisting of XylF, DnaK and P72. In a preferred embodiment, said active ingredient is a combination of XylF, DnaK and P72. It can be understood by a person having ordinary skill in the art that said active ingredient can be a recombinant protein, which may comprises the amino acid sequences of at least two proteins selected from a group consisting of XylF, DnaK and P72 provided that the structure of the epitope of each of XylF, DnaK and P72 is not influenced. In an alternative embodiment, said composition may comprise a mixture of said active ingredients, obtained by mixing at least two proteins selected from a group consisting of XylF, DnaK and P72.

Those having ordinary skill in the art can readily understand that if a vaccine contains two or more active ingredients, its effect is unpredictable, especially when said two or more active ingredients are against the same pathogen infection, because undesired result might occur due to interference between said two or more active ingredients with each other. In another aspect, even though said two or more active ingredients do not interfere with each other and no any undesired result occurred, there is still no motivation from the economic viewpoint to combine said two or more active ingredients in one single vaccine if combining said two or more active ingredients does not produce better effect (for example, higher immune response induction). In view of the above, combining two or more active ingredients in one single vaccine may have industrial benefits only when combination of said two or more active ingredients can produce better effect. However, without performing experiments, it is unpredictable what kind of candidate ingredients or compositions can produce better effect.

In an embodiment, said active ingredient of said composition has a concentration of 50 to 300 μg/mL, based on the total volume of said composition. In a preferred embodiment, said active ingredient of said composition is a combination of XylF, DnaK and P72, wherein each of XylF, DnaK and P72 has a concentration of 100 g/mL, based on the total volume of said composition. Those having ordinary skill in the art can readily understand that said concentration can be adjusted depending on the application purpose of the composition. For example, in order to make transportation and storage of the composition become more convenient, those having ordinary skill in the art can prepare said composition with higher concentration of said active ingredient (s), and dilute said composition just before use.

The term "adjuvant" has the same meaning as that well-known in medication/vaccine field. For example, said adjuvant is used for improving the immunogenic effect of said active ingredients, and/or stabilizing said active ingredients. Said adjuvant includes, but not limited to, complete Freund's adjuvant, incomplete Freund's adjuvant, alumina gel, surfactant, anionic polymer, peptide, oily emulsion, or a combination thereof. In an embodiment, said adjuvant is an alumina gel.

In another aspect of the present disclosure, the present disclosure provides an antigen expressing vector. The goal of the construction of said antigen expression vector is to express the active ingredient (i.e. a recombinant antigen) of said composition in a prokaryotic expression system so that mass production of said recombinant antigen is possible. Although there have been a lot of experiences in expressing proteins in prokaryotic expression system, different expression conditions may be needed for different proteins due to biodiversity. Therefore, it is still necessary to conduct a large amount of experiments to test the expression condition for any specified antigen. Through the researches of the present disclosure, an expression vector that can express recombinant antigens in a prokaryotic expression system was successfully constructed, preferably for *E coli* expression system. The expression vector of the present disclosure that can express recombinant antigens in *E coli* expression system can be easily modified by those having ordinary skill in the art, thereby allowing the expression vector of the present disclosure to express recombinant antigens in other prokaryotic expression systems.

In another aspect, one of the existing technical problems in production of said active ingredients is the purification of said active ingredients expressed from said prokaryotic expression system. The recombinant proteins expressed in a prokaryotic expression system usually have poor solubility, which increases the difficulty and cost of the isolation/purification step. In view of the above, the antigen expression vector of the present disclosure is designed to allow it to express a recombinant protein that have good solubility, thereby simplifying the step of isolation/purification of the recombinant protein and reducing the cost thereof.

The expression vector of the present disclosure comprises an expression element; a nucleotide sequence encoding said XylF, said DnaK, said P72, or a combination thereof; and a sequence encoding a fusion partner. In an embodiment, whereein said nucleotide sequence comprises SEQ ID NO: 04, SEQ ID NO: 05 or SEQ ID NO: 06, or a combination thereof. Those having ordinary skill in the art can modify said nucleotide sequence, depending on the codon preference of the selected prokaryotic expression system, as long as said nucleotide sequence can encode said XylF, said DnaK, said P72, or a combination thereof.

In a preferred embodiment, the research of the present disclosure has proved that DsbC of *E. coli*, MsyB of *E. coli*, FklB of *E. coli*, or a combination thereof is preferably used as fusion partner for expression of XylF, DnaK, P72 or a combination thereof, thereby making the recombinant proteins produced in a prokaryotic expression system have desired solubility. In another preferable embodiment, in order to facilitate the purification step, said expression vector may further comprise a sequence encoding His-tag, GST-tag or a combination thereof, thereby the obtained recombinant proteins can be purified by passing through a nickel ion affinity column or a glutathione affinity column.

In an embodiment, said expression element at least comprises a promoter and a ribosome binding site for performing transcription and/or translation. In another embodiment, to facilitate genetic engineering operation, said expression vector may further comprise a multiple cloning site consisting of restriction enzyme cutting sites, a selectable marker or a combination thereof. Said selectable marker can be an antibiotic-resistant gene or an auxotrophic gene.

In another aspect, the present disclosure provides a method of production of a soluble protein, wherein said soluble protein is XylF, DnaK, P72 or a combination thereof. The method of the present disclosure comprises (1) providing a prokaryotic expression system; and (2) expressing an antigen gene in the expression vector in said prokaryotic expression system. The term "soluble" in this text refers a property that said protein tends to dissolve in an aqueous solution. The term "expression" in this text indicates the expression vector is induced to transcribe and translate the target gene in the aforesaid prokaryotic expression system by any means. The means might be, but not limited to, addition of isopropyl-β-D-thiogalactoside (IPTG) to said prokaryotic expression system.

Example 1 Investigation of Proteins Suitable as the Active Ingredients of the Composition of the Present Disclosure (1) Preparation of an Inactivated *Mycoplasma hyorhinis* Vaccine

*Mycoplasma hyorhinis* (ATIT-7) was cultured in well-known Friis medium and then used to prepare an inactivated *Mycoplasma hyorhinis* vaccine according to the method as disclosed in Taiwan Invention Patent No. 1238721.

(2) Preparation of the Antiserum Directed to *Mycoplasma hyorhinis*

Three of 4-week old SPF pigs were purchased from the second-generation SPF piggery in Animal Technology Laboratories of Agricultural Technology Research Institute. All pigs were fed under the same raising condition in the house for experimental SPF pigs. The pigs were raised to 32 days, 46 days and 60 days of age, respectively, and at each of the above time points, 2 mL of inactivated *Mycoplasma hyorhinis* vaccine was administered to the pigs by intramuscular injection. When the pigs were raised to 74 days of age, blood samples were taken from the jugular veins of the pigs and placed at room temperature (about 25° C.) for 1 hour. The blood samples then stayed at 4° C. Next day, the blood samples were centrifuged at 1,107×g for 30 min. The supernatant (namely, the antiserum) was transferred into a clean centrifuge tube and stored at −20° C. for use in the subsequent steps.

(3) Extraction of the Total Proteins of *Mycoplasma hyorhinis*

The total proteins were extracted from *Mycoplasma hyorhinis* by using a protein extraction kit (Ready Prep™ protein extraction kit; Bio-Rad, USA). First, *Mycoplasma hyorhinis* cultured in Friis medium was centrifuged (10,000×g, 20 min.) to collect bacterial cells. The bacterial cells, after washed 3 times by a low-salt buffer solution (100 mM Tris-base, 250 mM sucrose, pH 8.0), were suspended in 1 mL of sample buffer (complete 2-D rehydration/sample buffer) with addition of 10 μL of TBF reducing agent (ReadyPrep™ TBP reducing agent), an appropriate amount of Bio-Lyte 3/10 ampholyte (the final concentration of ampholyte is 0.2%) and an appropriate amount of a protease inhibitor. The bacterial cells were disrupted by ultrasonication. The disrupted cells were removed by centrifuging and the supernatant, which contained the total proteins of *Mycoplasma hyorhinis*, was reserved and used in the subsequent steps.

The concentration of the total proteins was determined by a protein assay kit (RC DC™ Protein Assay Kit; Bio-Rad, USA). 100 μL of said supernatant containing the total proteins were mixed thoroughly with 500 μL of RC reagent I, and the mixture was placed at room temperature (about 25° C.) and allowed the reaction to proceed for 1 min. 500 μL of RC reagent II was then added, mixed thoroughly and centrifuged (15,000×g, 5 min.). The precipitants were collected, and then mixed with 510 μL of Reagent A' thoroughly. The mixture was placed at room temperature (about 25° C.) and allowed the reaction to proceed for 5 min or until all precipitants were dissolved. Thereafter, 4 mL of Reagent B was added and the mixture was again placed at room temperature (about 25° C.) and allowed the reaction to proceed for 15 min. The absorbance of the solution at a wavelength of 750 nm was determined by a spectrophotometer. Bovine serum albumin (BSA) was used as a standard sample to establish a standard curve of protein concentration vs absorbance. The concentration of the total proteins in said supernatant can be obtained by interpolating the absorbance of the supernatant sample on the standard curve and calculating the concentration of the total proteins therein. The sample with known concentration of the total proteins would be used in the subsequent protein electrophoresis step.

(4) Two-Dimensional Electrophoresis of the Proteins

Two-dimensional electrophoresis of the proteins comprises two steps: isoelectric focusing (IEF) electrophoresis and sodium dodecyl sulfate-polyacrylamide gel electrophoresis (SDS-PAGE), as stated in the following paragraphs.

Isoelectric Focusing (IEF) Electrophoresis

Isoelectric focusing (IEF) electrophoresis a technique for separating different proteins by differences in their isoelectric points. First, 1 mg of the supernatant containing the total proteins of *Mycoplasma hyorhinis* was taken and mixed with an appropriate amount of rehydration buffer in such a way that the total volume of the resulting mixture was 400 μL. Next, the mixture was added into the sample slots of a focusing tray (Bio-Rad, USA). Two pieces of filter paper that had been wetted with distilled-deionized water were placed respectively on the positive electrode and the negative electrode. Said filter paper could adsorb impurities and salts in the sample, thereby avoiding the influence of said impurities and salts on the subsequent experiment and damage of the electrodes. An IPG gel strip, namely ReadyStrip™ (pH 5-8/17 cm) was then put slowly into the focusing tray. 2.5 mL of mineral oil was taken and spread evenly on the IPG gel strip to avoid evaporation of the sample, which might influence on the subsequent experiment. The focusing tray was covered with a top lid and placed on PROTEAN IEF cell of an isoelectric focusing electrophoresis instrument (Bio-Rad, USA). After the program for PROTEAN IEF cell had been set, one dimensional electrophoresis was conducted in 5 stages. The first stage is rehydration at 50 V for 12 hours, to make the sample absorbed by the IPG gel strip. The second stage is removal of salt ions and impurities at 250 V for 15 min. The third stage is elevation of voltage, wherein the voltage was linearly elevated to a focusing voltage of 10,000 V over 4 hours. The fourth stage was an isoelectric focusing step conducted at 50,000V×hr. The fifth stage was maintenance of voltage at 500V to avoid excess reaction. After completion of the one dimensional electrophoresis, the IPG gel strip could be storage at −80° C., or after equilibrated, promptly used in the subsequent SDS-PAGE step.

Sodium Dodecyl Sulfate-Polyacrylamide Gel Electrophoresis (SDS-PAGE)

Sodium dodecyl sulfate-polyacrylamide gel electrophoresis is a technique for separating different proteins by differences in their molecular weight. First, after the IPG gel strip was washed with deionized water, the mineral oil and water on the back side of the gel side were absorbed off by filter paper. Then, the IPG gel strip was placed in a disposable rehydration tray. 6 mL of Equilibrating Buffer I (6M urea, 2% SDS, 0.375 M Tris, 20% glycerin, 130 mM DTT, pH 8.8) was added thereto and the resulting mixture was shaken for 20 min. The IPG gel strip was then taken out and Equilibrating Buffer I left on the back side of the gel side were absorbed off by filter paper. The IPG gel strip was again placed in a disposable rehydration tray. 6 mL of Equilibrating Buffer II (6 M urea, 2% SDS, 0.375 M Tris, 20% glycerin, 135 mM iodoacetamide, pH 8.8) was added thereto and the resulting mixture was shaken for 20 min. After completing said equilibrating treatment, SDS-PAGE was conducted.

First, 12.5% of separating gel was prepared. The IPG gel strip was placed on the top surface of the separating gel. An appropriate amount of dissolved agarose (ReadyPrep™ Overlay Agarose, Bio-Rad, USA) was then added thereto. To make the determination of the molecular weight more convenient, the filter paper with protein molecular weight standards dotted thereon was placed beside the IPG gel strip. After coagulation of agarose, the gel strip and the filter paper with protein molecular weight standards were fixed on the separating gel. The electrophoresis gel piece was placed in an electrophoresis vessel (Bio-Rad, USA) and an electrophoresis buffer (25 mM Tris, 192 mM glycine, 0.1% SDS, pH 8.3) was introduced into the vessel. Electrophoresis was conducted at an electric current of 26 mA for 15 hours, thereby separating the proteins with different molecular weight.

(5) Western Blotting Method

After protein electrophoresis, the aforesaid gel piece was immersed in a blotting buffer [25 mM Tris base, 192 mM glycine, 10% (v/v), methanol, pH 8.3]. PVDF film was cut to a proper size and immersed in methanol for several seconds, then washed 1 time with deionized water and immersed in the blotting buffer. After the gel piece and the PVDF film had immersed in the blotting buffer for 15 min, a piece of filter paper, the gel piece, the PVDF film and another piece of filter paper were put sequentially into a blotting transfer apparatus and transferring was conducted at an electric current of 1,300 mA for 1.5 hours.

After completion of transferring, said PVDF film was immersed in a blocking buffer [20 mM Tris-base, 150 mM NaCl, 5% (w/v) skim milk, pH 7.4] at room temperature for 1 hour. An appropriate amount of the antiserum (1,000 times dilution) against *Mycoplasma hyorhinis* prepared in the above experiment was added and shaken at room temperature for 1 hour. After the blocking solution was poured off and said PVDF film was washed with an appropriate amount of TBST Buffer [20 mM Tris-base, 150 mM NaCl, 0.05% (v/v) Tween-20, pH 7.4] 3 times (5 min/time), a blocking buffer containing alkaline phosphatase-conjugated goat anti-pig IgG (H+L) (2,000 times dilution) was added. After shaken in the dark for 1 hour, said PVDF film was washed with TBST Buffer 3 times, and then NBT/BCIP solution (Thermo Fisher Scientific, USA) was added to induce a color development reaction.

(6) Identification of Proteins

The colored dots (17 dots in total, not shown in the figures), as shown by the result of the color development reaction in said western blotting method, indicated the *Mycoplasma hyorhinis* proteins capable of reacting with the antiserum against *Mycoplasma hyorhinis*. Comparing the aforesaid result of the color development reaction with the gel piece that had been subjected to electrophoresis, the bands of the gel piece, which were at the position corresponding to the position of the colored dots, was taken by a micropipette and used in mass spectrum analysis. Identification of the proteins obtained from the above were conducted by comparing their amino acid sequences with protein sequence database. As a result, 3 proteins were identified, namely XylF, DnaK and P72, which respectively have the sequences as shown in SEQ ID NO: 01, SEQ ID NO: 02, and SEQ ID NO: 03. The present disclosure proceeded subsequent research on these 3 proteins.

Example 2 Construction of the Expression Vector of the Present Disclosure (1) Point Mutation and Cloning of Antigen Genes According to the data of National Center for Biotechnology Information (NCBI) of America, the sequences of said XylF, DnaK and P72 genes respectively had 4, 1 and 8 TGA codons. TGA codon was considered as stop codon in *E. coli* expression system. To avoid that *E. coli* expression system couldn't produce the full-length of the aforesaid proteins, TGA codons in the sequences of the antigen genes were mutated to TGG codons by polymerase chain reaction.

Extraction of the Genomic DNA of *Mycoplasma hyorhinis*

The genomic DNA of *Mycoplasma hyorhinis* was extracted by utilizing a DNA purification kit (Tissue & Cell Genomic DNA Purification kit; GMbiolab, Taiwan). First, 4.5 mL of the liquid culture of *Mycoplasma hyorhinis* was taken and put into a centrifuge tube. After centrifuging (5,870×g, 5 min), the supernatant was poured off and the pellet was collected. Next, 20 μL of protease K (10 mg/mL) and 200 μL of extraction reagent were added and allowed to react at 56° C. for 3 hours. 200 μL of binding solution was added and allowed to react at 70° C. for 10 min. After completion of the reaction, 200 μL of absolute alcohol was added and transferred into a micro-centrifuge tube and mixed thoroughly, the resulting solution (including precipitate) was pipetted into a spin column and the spin column was then put into a collection tube. After centrifuging (17,970×g) for 2 min, the supernatant was poured off and 300 μL of binding reagent was again added into the spin column. After centrifuging (17,970×g) for 2 min, the supernatant was poured off. 700 μL of wash solution was added into the spin column and the mixture was centrifuged (17,970×g) for 2 min, and then the supernatant was poured off. The above wash step was repeated one time. At last, the mixture was centrifuged at 17,970×g for 5 min to remove residual alcohol. The spin column was put into a sterilized micro-centrifuge tube and an appropriate amount of sterile deionized water was added to drain the genomic DNA.

Point Mutation of XylF Antigen Gene

Primers XylF/XylR and mutation primers XylM1 to XylM8 for XylF antigen gene were designed, and the sequences of these primers were listed in Table 1.

TABLE 1

| SEQ ID NO | Primer | Sequence (5' to 3') |
|---|---|---|
| SEQ ID NO: 10 | XylF | GATATAGGATCCTCATTTGTAGCTTGTGGAACAACAG |
| SEQ ID NO: 11 | XylR | CAATATGTCGACTTGTGTTACACCATTAGTTGGTACTGTACC |
| SEQ ID NO: 12 | XylM1 | GATCCAGATAATCCAAGATGGATTAATGCACAAAAAGATA |
| SEQ ID NO: 13 | XylM2 | TATCTTTTTGTGCATTAATCCATCTTGGATTATCTGGATC |
| SEQ ID NO: 14 | XylM3 | CAAAATGCACAAAACAACTGGTTAACTCAACAAGCAAACT |
| SEQ ID NO: 15 | XylM4 | AGTTTGCTTGTTGAGTTAACCAGTTGTTTTGTGCATTTTG |
| SEQ ID NO: 16 | XylM5 | GGTTCAACTTCATATGATTGGTATGTTTCTTACGATAATG |
| SEQ ID NO: 17 | XylM6 | CATTATCGTAAGAAACATACCAATCATATGAAGTTGAACC |
| SEQ ID NO: 18 | XylM7 | TTATGTTCCAGGATGGAATTACGGAGACGCTG |
| SEQ ID NO: 19 | XylM8 | CAGCGTCTCCGTAATTCCATCCTGGAACATAA |

Using the genomic DNA of *Mycoplasma hyorhinis* as templates, the DNA fragments were amplified by using primer pairs XylF/XylM2, XylM1/XylM4, XylM3/XylM6, XylM5/XylM8, and XylM7/XylR etc., respectively. 50 μL of the reaction mixture of PCR contained 1×GDP-HiFi PCR buffer B, 200 μM dNTP (dATP, dTTP, dGTP and dCTP), 1 μM primers for amplification, 200 ng of the genomic DNA of *Mycoplasma hyorhinis* and 1 U GDP-HiFi DNA polymerase. The reaction condition of PCR is 96° C. for 5 min (one step); 94° C. for 30 sec, 55° C. for 30 sec, 68° C. for 30 sec (35 cycles); and 68° C. for 5 min (one step).

After completion of PCR, agarose gel electrophoresis was conducted to confirm whether there exist DNA fragments with predicted sizes. PCR products were recovered by Gel-M™ gel extraction system kit. Gene amplification was conducted by using 5 recovered PCR products as templates and using a primer pair of XylF/XylR. The reaction condition of PCR is 96° C. for 2 min (one step); 94° C. for 30 sec, 55° C. for 30 sec, 68° C. for 45 sec (35 cycles); and 68° C. for 5 min (one step). XylF gene with point mutation was obtained by said PCR. The products of PCR were recovered by PCR-M™ Clean Up system kit. According to the result of sequence determination, the XylF gene of the present disclosure had a nucleotide sequence as shown in SEQ ID NO: 4.

Point Mutation of DnaK Antigen Gene

Pimers DnaKF/DnaKR and mutation primers DnaKM1 to DnaKM2 for DnaK antigen gene were designed, and the sequences of these primers were listed in Table 2.

TABLE 2

| SEQ ID NO | Primer | Sequence (5' to 3') |
|---|---|---|
| SEQ ID NO: 20 | DnaKF | GATATAGGATCCATGGCAAAAGAAATTATTTTAGGAATAGATTTAG |
| SEQ ID NO: 21 | DnaKR | CAATATGTCGACTTAATTTTCTTTAACTTCAGCTTCAATTGGTTG |
| SEQ ID NO: 22 | DnaKM1 | GATGACTGTGATCATGTTATTGTTGATTGGTTAGTTGACAAAATTAA AAAAGAATATG |
| SEQ ID NO: 23 | DnaKM2 | CATATTCTTTTTTAATTTTGTCAACTAACCAATCAACAATAACATGAT CACAGTCATC |

Using the genomic DNA of *Mycoplasma hyorhinis* as templates, the DNA fragments were amplified by respectively using primer pairs DnaKF/DnaK M2 and DnaKM1/DnaKR. 50 μL of the reaction mixture of PCR contained 1×GDP-HiFi PCR buffer B, 200 LM dNTP (dATP, dTTP, dGTP, and dCTP), 1 LM primers for amplification, 200 ng of the genomic DNA of *Mycoplasma hyorhinis* and 1 U GDP-HiFi DNA polymerase. The reaction condition of PCR is 96° C. for 5 min (one step); 94° C. for 30 sec, 55° C. for 30 sec, 68° C. for 30 sec (35 cycles); and 68° C. for 5 min (one step).

After completion of PCR, agarose gel electrophoresis was conducted to confirm if there were DNA fragments with predicted sizes. PCR products were recovered by Gel-M™ gel extraction system kit. Gene amplification was conducted by using 2 recovered PCR products as templates and using a primer pair of DnaKF/DnaK. The reaction condition of PCR is 96° C. for 2 min (one step); 94° C. for 30 sec, 55° C. for 30 sec, 68° C. for 45 sec (35 cycles); and 68° C. for 5 min (one step). DnaK gene with point mutation was obtained by said PCR. Finally, the products of PCR were recovered by PCR-M™ Clean Up system kit. According to the result of sequence determination, the DnaK gene of the present disclosure had a nucleotide sequence as shown in SEQ ID NO: 5.

Point Mutation of P72 Gene

Primers P72F/P72R and mutation primers P72M1 to P72M8 for P72 antigen gene, were designed, and the sequences of these primers were listed in Table 3.

TABLE 3

| SEQ ID NO | Primer | Sequence (5'to 3') |
|---|---|---|
| SEQ ID NO: 24 | P72F | CAATATGGATCCTCTTGTGGACAACCAACCACAATTAAATTTG |
| SEQ ID NO: 25 | P72R | GTATAAGTCGACTTAGTGATGGTGATGGTGATGAGCTGCAGATTT TTCGGCCATAAAATC |
| SEQ ID NO: 26 | P72M1 | CTTCTCAAGGTTCATATTGGCCAATGATGCTAGGAATG |
| SEQ ID NO: 27 | P72M2 | CATTCCTAGCATCATTGGCCAATATGAACCTTGAGAAG |
| SEQ ID NO: 28 | P72M3 | ACTAAGCAAAGCTCTGATTGGAATCTTATTTTAGGAAACA |
| SEQ ID NO: 29 | P72M4 | TGTTTCCTAAAATAAGATTCCAATCAGAGCTTTGCTTAGT |
| SEQ ID NO: 30 | P72M5 | CTTTCTAAAACTAATAAAACTTTTTGGAGTGAAAAAAGTTTACAA AATAACAA |
| SEQ ID NO: 31 | P72M6 | TTGTTATTTTGTAAACTTTTTTCACTCCAAAAAGTTTTATTAGTTTT AGAAAG |
| SEQ ID NO: 32 | P72M7 | GTTGAAAACCAATATCAAGAATGGGAAAACACTTTAAAACAAAC AC |
| SEQ ID NO: 33 | P72M8 | GTGTTTGTTTTAAAGTGTTTTCCCATTCTTGATATTGGTTTTCAAC |
| SEQ ID NO: 34 | P72M9 | CAAGCAAATACTGAAACTACTTCATGGACAAAAAAAGATATTCA AACTAAATC |
| SEQ ID NO: 35 | P72M10 | GATTTAGTTTGAATATCTTTTTTTGTCCATGAAGTAGTTTCAGTAT TTGCTTG |
| SEQ ID NO: 36 | P72M11 | CTGAATACTTTAAACCTATAAATCAATGGGGATCTTTTGAAATTA GACAATATTTAAC |
| SEQ ID NO: 37 | P72M12 | GTTAAATATTGTCTAATTTCAAAAGATCCCCATTGATTTATAGGTT TAAAGTATTCAG |
| SEQ ID NO: 38 | P72M13 | CTATTCTGTAGATTCTCCTTGGTCACGTGCATTTTTTAAAAAAG |
| SEQ ID NO: 39 | P72M14 | CTTTTTTAAAAAATGCACGTGACCAAGGAGAATCTACAGAATAG |

TABLE 3-continued

| SEQ ID NO | Primer | Sequence (5'to 3') |
|---|---|---|
| SEQ ID NO: 40 | P72M15 | GAAAACAAAAAGCTTCAGAATGGACAACAAGAGAAGATGTTAT G |
| SEQ ID NO: 41 | P72M16 | CATAAACATCTTCTCTTGTTGTCCATTCTGAAGCTTTTTGTTTTC |

Using the genomic DNA of *Mycoplasma hyorhinis* as templates, the DNA fragments were amplified by respectively using primer pairs P72F/P72M2, P72M1/P72M4, P72M3/P72M6, P72M5/P72M8, P72M7/P72M10, P72M9/P72M12, P72M11/P72M14, P72M13/P72M16, and P72M15/P72R. 50 μL of the reaction mixture of PCR contained 1×GDP-HiFi PCR buffer B, 200 μM dNTP (dATP, dTTP, dGTP, and dCTP), 1 μM primers for amplification, 200 ng of the genomic DNA of *Mycoplasma hyorhinis* and 1 U GDP-HiFi DNA polymerase. The reaction condition of PCR is 96° C. for 5 min (one step); 94° C. for 30 sec, 55° C. for 30 sec, 68° C. for 30 sec (35 cycles); and 68° C. for 5 min (one step).

After completion of PCR, agarose gel electrophoresis was conducted to confirm if there were DNA fragments with predicted sizes. PCR products were recovered by Gel-M™ gel extraction system kit. Gene amplification was conducted by using 9 recovered PCR products as templates and using a primer pair of P72F/P72R. The reaction condition of PCR is 96° C. for 2 min (one step); 94° C. for 30 sec, 55° C. for 30 sec, 68° C. for 1 min (35 cycles); and 68° C. for 5 min (one step). P72 gene with point mutation was obtained by said PCR. Finally, the products of PCR were recovered by PCR-M™ Clean Up system kit. According to the result of sequence determination, the P72 gene of the present disclosure had a nucleotide sequence as shown in SEQ ID NO: 6.

(2) Construction of the Expression Vectors for *Mycoplasma hyorhinis* Antigens

The expression vectors for *Mycoplasma hyorhinis* antigens were constructed by using the vectors containing various fusion partner genes as backbone. The fusion partner genes were respectively the DNA sequences of DsbC, MsyB, FklB of *E. coli*. The construction schedule for said expression vectors were as follows.

XylF gene, DnaK gene and P72 gene of the present disclosure prepared in the above experiments were respectively cut by BamHI and SalI, and then, by using T4 DNA ligase, the DNA fragments obtained above were respectively ligated to the DsbC gene-fused expression vector, MsyB gene-fused expression vector or FklB gene-fused expression vector that had been cut with the same restriction enzymes. Thereafter, the ligated products were transformed into *E. coli* ECOS 9-5. The transformed strains were selected by colony PCR. DNA electrophoresis was conducted to confirm whether there existed DNA fragments with predicted sizes. After confirming that the recombinant vectors from the transformed strains carried inserted DNA, the vectors were extracted from the transformed strains and the DNA sequences thereof were determined. The vectors with correct DNA sequences were respectively named pET-DsbC-XylF (SEQ ID NO: 07), pET-MysB-DnaK (SEQ ID NO: 08), and pET-FklB-P72 (SEQ ID NO: 09).

Example 3 Preparation and Application of the Subunit Vaccine of the Present Disclosure (1) Expression of the Recombinant Antigens by the Expression Vectors of the Present Disclosure The vector for expressing *Mycoplasma hyorhinis* antigens was transformed into *E. coli* BL21 (DE3). A single colony of the strain expressing the antigens was selected and inoculated in 12 mL of LB medium containing kanamycin (final concentration: 30 μg/mL), then was cultured at 37° C. and under the condition of 180 rpm overnight. Thereafter, 10 mL of the liquid culture of *E. coli* was taken and added to 1 L of LB medium containing kanamycin (final concentration: 30 μg/mL) and was shake-cultured (37° C., 180 rpm) until $OD_{600}$ achieved about 0.4-0.6. 0.1 mM IPTG was then added at 28° C. to induce protein expression. After induction for 4 hours, the culture was centrifuged (10,000×g, 10 min, 4° C.) to collect bacterial cells. After the bacterial cells were resuspended in 10 mL of phosphate buffer (20 mM sodium phosphate, 500 mM NaCl, pH 7.4) and were disrupted by ultrasonication, the suspension was centrifuged (30,966×g, 30 min) to collect the supernatant. Finally, the supernatant was filtered through a filter membrane with 0.22 μM pore size and the filtrate was collected. Protein electrophoresis was conducted to observe the expression status and solubility of the recombinant antigens. The result was shown in FIG. 1. It could be observed from FIG. 1 that the recombinant antigens of the present disclosure were well-expressed in *E. coli*. Besides, the recombinant antigens of the present disclosure had excellent solubility, indicating that the fusion partners selected by the present disclosure were appropriate.

Figure 2:
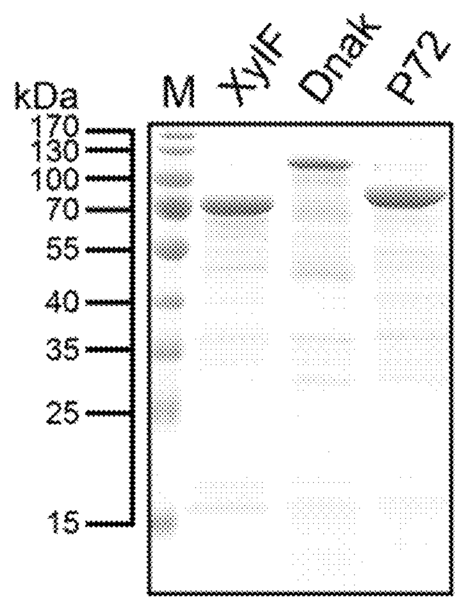
FIG. 2 shows the result of protein electrophoresis conducted in Example 3 for observing the purification of the recombinant antigen of the present disclosure.

Afterward, immobilized-metal ion affinity chromatography was used for protein purification through the covalent bonding between His tag on the recombinant antigens and nickel ions or cobalt ions. The recombinant antigens were purified by AKTA prime plus (GE Healthcare, Sweden) equipped with 5 mL HiTrap™ Ni excel column (GE Healthcare, Sweden). First, the aforesaid supernatant was introduced into HiTrap™ Ni excel column after the column was equilibrated with 25 mL of phosphate buffer solution. After completing introduction of sample, 100 mL of a wash buffer solution containing 30 mM imidazole (20 mM sodium phosphate, 500 mM NaCl, 30 mM imidazole, pH 7.4) was used to wash the column so that the non-specific proteins adhered thereon can be removed. Finally, 150 mL of an elution buffer solution containing 250 mM imidazole (20 mM sodium phosphate, 500 mM NaCl, 250 mM imidazole, pH7.4) was used to wash off the recombinant antigens from the resin, wherein imidazole of high concentration can compete the binding site on the resin with the recombinant antigens and thereby cause the recombinant antigens being washed off. The purified antigen solution was put into Amicon™ ultra-15 ultracel-30K centrifuge tube (Merck Millipore, USA), centrifuged (2,600×g) below 4° C., adjusted to an appropriate volume, and then stored at 4° C. for use in the subsequent step. The result of purification was shown in FIG. 2. From FIG. 2, it can be seen that the recombinant antigens of the present disclosure obtained in this experiment had high purity.

(2) Preparation of the Subunit Vaccine of the Present Disclosure and Test of the Protective Immune Response Thereof Under the conditions as shown in Tables in the following paragraphs, the recombinant antigens of the present disclosure prepared in the above experiment were respectively well-mixed with an adjuvant (alumina gel), thereby preparing various subunit vaccines containing single antigen and cocktail vaccines containing multiple antigens. The dosage of the vaccine was 2 mL/dose, wherein the content of each recombinant antigen contained in the vaccine was 200 μg.

Experiment 1 for Determination of the Protective Immune Response of the Single Antigen Vaccine This experiment was conducted in the house for genetically modified organisms (GMOs) in Animal Drugs Inspection Branch of Animal Health Research Institute. 12 of 3-week old pigs that had been tested negative for antibody against *Mycoplasma hyorhinis*, were randomly separated into groups A to D. There were 3 pigs in each group, wherein groups A to C were experiment groups and D group was a control group. The pigs of groups A to C were each immunized with the vaccine of this experiment via intramuscular injection (2 mL/dose) once, respectively at 3-week of age and 5-week of age. The pigs of group D were not immunized. The components of the vaccines were as shown in Table 4.

TABLE 4

| | | Component/dose | | |
|---|---|---|---|---|
| group | vaccine | XylF (μg) | DnaK (μg) | P72 (μg) |
| A group | V-001 | 200 | — | — |
| B group | V-002 | — | 200 | — |
| C group | V-003 | — | — | 200 |
| D group | — | — | — | — |

When the pigs were 7-week old (namely, 2 weeks after immunization), abdominal challenge test was conducted by using the culture medium containing isolated wild strain ATIT-2 of *Mycoplasma hyorhinis*. When the pigs were 10-week old (namely, 3 weeks after challenge test), anatomical pathology examination was conducted. The percentages of pathological changes such as peritonitis, pleurisy, pericarditis and joint swelling etc. were calculated. Visible pathological changes were scored according to the method of Magnusson et al. (Vet. Immunol. Immunopathol., 61:83-96, 1998).

The result of the experiment was shown in Table 5. The subunit vaccine prepared from XylF can reduce the incidence of swine peritonitis and pleurisy, in addition, the average scores of pathologic changes for immunized pigs were lower than those for the unimmunized pigs (control group), indicating that XylF can induce significant protective immune response. The subunit vaccines prepared from DnaK and P72 can respectively reduce the incidence of peritonitis and pleurisy.

It's worth noting that the data in Table 5 should not be interpreted as that the subunit vaccine prepared from XylF is advantageous only in alleviating peritonitis and pleurisy, but merely indicates that the subunit vaccine prepared from XylF has a less notable effect in alleviating other conditions during the experiment. For the same reason, the data in Table 5 should not be interpreted as that the subunit vaccines prepared from DnaK and from P72 are advantageous respectively in alleviating peritonitis and pleurisy only, but merely indicates that the subunit vaccine prepared from DnaK or from P72 has a less notable effect in alleviating other conditions during the experiment.

TABLE 5

| | Score of pathologic changes | | | | | |
|---|---|---|---|---|---|---|
| Group | Peritonitis | Pleurisy | Pericarditis | Joint swelling | Total score | Average score |
| A | 1 | 0 | 2 | 4 | 7 | 2.3 |
| B | 1 | 4 | 3 | 7 | 15 | 5 |
| C | 3 | 0 | 0 | 8 | 11 | 3.6 |
| D | 3 | 3 | 0 | 4 | 10 | 3.3 |

Experiment 2 for Determination of the Protective Immune Response of the Cocktail Vaccine This experiment was conducted in the house for genetically modified organisms (GMOs) in Animal Drugs Inspection Branch of Animal Health Research Institute. 24 of 4-week old pigs that had been tested negative for antibody against *Mycoplasma hyorhinis* were selected and randomly separated into 2 groups, namely immunization group (group E) and control group (group F). There were 12 pigs in each group. The pigs of immunization group were each immunized with the vaccine of this experiment via intramuscular injection (2 mL/dose) once, respectively at 4 week of age and 6 week of age. The pigs of the control group were not immunized. The components of the vaccine were as shown in Table 6.

TABLE 6

| | Component/Dose | | | |
|---|---|---|---|---|
| Group | Vaccine | XylF (μg) | DnaK (μg) | P72 (μg) |
| E group | V-004 | 200 | 200 | 200 |
| F group | — | — | — | — |

The result of the experiment was shown in Table 7. The cocktail vaccine of the present disclosure (comprising a mixture of 3 recombinant antigens of the present disclosure in this experiment) could significantly alleviate the clinical symptoms of peritonitis, pleurisy, pericarditis and joint swelling etc. caused by *Mycoplasma hyorhinis* infection, and showed better effect when compared with the effect of the subunit vaccine containing single antigen (as stated in Table 5).

TABLE 7

| | Score of pathologic changes | | | | | |
|---|---|---|---|---|---|---|
| Group | Peritonitis | Pleurisy | Pericarditis | Joint swelling | Total score | Average score |
| E | 8 | 10 | 8 | 9 | 35 | 2.9 |
| F | 18 | 16 | 12 | 23 | 69 | 5.8 |

What is claimed is:

1. A composition for avoiding a disease caused by *Mycoplasma hyorhinis* infection, comprising
   an active ingredient comprising XylF, DnaK, P72 or a combination thereof; and
   an adjuvant;
   wherein said XylF comprises SEQ ID NO: 01, said DnaK comprises SEQ ID NO: 02, and said P72 comprises SEQ ID NO: 03;
   wherein said disease is at least one selected from peritonitis, pleurisy, pericarditis and joint swelling.

2. The composition of claim 1, wherein said active ingredient comprises at least two selected from a group consisting of XylF, DnaK and P72.

3. The composition of claim 2, wherein said active ingredient comprises a combination of XylF, DnaK and P72.

4. The composition of claim 1, wherein said active ingredient has a concentration of 50 to 300 μg/mL, based on the total volume of said composition.

5. The composition of claim 1, wherein said adjuvant comprises complete Freund's adjuvant, incomplete Freund's adjuvant, alumina gel, surfactant, anionic polymer, peptide, oily emulsion, or a combination thereof.

6. The composition of claim 1, wherein said disease is peritonitis, pleurisy or a combination thereof provided that said active ingredient is XylF.

7. The composition of claim 1, wherein said disease is peritonitis provided that said active ingredient is DnaK.

8. The composition of claim 1, wherein said disease is pleurisy provided that said active ingredient is P72.

9. The composition of claim 1, wherein said disease is peritonitis, pleurisy, pericarditis and joint swelling provided that said active ingredient is a combination of XylF, DnaK and P72.

10. An expression vector for production of the active ingredient of the composition of claim 1 in a prokaryotic expression system, comprising:
   an expression element, comprising a promoter and a ribosome binding site;
   a nucleotide sequence encoding said XylF, said DnaK, said P72, or a combination thereof; and
   a sequence encoding a fusion partner;
   wherein said nucleotide sequence comprises SEQ ID NO: 04, SEQ ID NO: 05 or SEQ ID NO: 06, or a combination thereof.

11. The expression vector of claim 10, wherein said fusion partner is DsbC of *E. coli*, MsyB of *E. coli*, FklB of *E. coli*, or a combination thereof.

12. The expression vector of claim 11, wherein
   said fusion partner is DsbC of *E. coli* provided that said nucleotide sequence encodes XylF;
   said fusion partner is MsyB of *E. coli* provided that said nucleotide sequence encodes DnaK; or
   said fusion partner is FklB of *E. coli* provided that said nucleotide sequence encodes P72.

13. The expression vector of claim 10, further comprising a sequence encoding histidine tag, glutathione S-transferase tag or a combination thereof.

14. The expression vector of claim 10, comprising a nucleotide sequence as shown in SEQ ID NO: 07, SEQ ID NO: 08, or SEQ ID NO: 09.

15. The expression vector of claim 10, wherein said prokaryotic expression system is *E. coli* expression system.

16. A method for production of a soluble protein, wherein said protein is XylF, DnaK, P72, or a combination thereof; wherein said method comprising
   providing a prokaryotic expression system; and
   expressing said nucleotide sequence of the expression vector of claim 10 in said prokaryotic expression system.

17. The method of claim 16, further comprising a step of passing a product obtained in the above step (2) through a nickel ion affinity column or a glutathione affinity column to obtain said soluble protein.

* * * * *

SEQUENCE LISTING

<160> NUMBER OF SEQ ID NOS: 41

<210> SEQ ID NO 1
<211> LENGTH: 447
<212> TYPE: PRT
<213> ORGANISM: Mycoplasma hyorhinis

<400> SEQUENCE: 1

Met Lys Lys Leu Ile Thr Lys Lys Phe Leu Tyr Leu Ser Thr Ile Ser
1 5 10 15

Thr Ala Ser Phe Ile Ala Phe Ala Ser Phe Val Ala Cys Gly Thr Thr
20 25 30

Ala Thr Gly Leu Ser Gln Thr Lys Asp His Ala Val Thr Asn Glu Ser
35 40 45

Ile Arg Val Ala Leu Thr Asp Pro Asp Asn Pro Arg Trp Ile Asn Ala
50 55 60

Gln Lys Asp Ile Leu Asn Tyr Ile Asp Lys Thr Glu Gly Ala Ile Ser
65 70 75 80

Thr Ile Thr Lys Asp Gln Asn Ala Gln Asn Asn Trp Leu Thr Gln Gln
85 90 95

Ala Asn Leu Asn Pro Ala Pro Lys Gly Phe Ile Ile Ala Pro Glu Asn
100 105 110

Gly Gly Gly Val Gly Thr Ala Val Asn Ser Ile Ala Glu Lys Asn Ile
115 120 125

Pro Ile Val Ala Tyr Asp Arg Leu Ile Thr Gly Ser Thr Ser Tyr Asp
130 135 140

Trp Tyr Val Ser Tyr Asp Asn Glu Lys Val Gly Glu Leu Gln Gly Leu
145 150 155 160

Ser Leu Ala Ala Gly Leu Leu Gly Lys Thr Asp Gly Ala Phe Lys Asp
165 170 175

Glu Thr Glu Met Leu Asn Tyr Leu Lys Asp His Met Pro Gln Glu Thr
180 185 190

Val Ser Phe Tyr Ala Val Ala Gly Ser Gln Asp Asp Asn Asn Ser Gln
195 200 205

Tyr Phe Tyr Asn Gly Ala Met Lys Ile Leu Lys Lys Leu Met Glu Asn
210 215 220

Ser Asn Gly Lys Val Val Asp Leu Ser Pro Arg Gly Asn Ala Val Tyr
225 230 235 240

Val Pro Gly Trp Asn Tyr Gly Asp Ala Gly Gln Arg Ile Gln Gln Phe
245 250 255

Phe Thr Gln Tyr Arg Asp Ser Ser Val Pro Asn Gly Val Leu Pro Val
260 265 270

Thr Tyr Asp Asn Val Thr Ile Pro Lys Ser Val Leu Lys Gly Phe Leu
275 280 285

Ala Pro Asn Asp Gly Met Ala Glu Gln Ala Val Asp Lys Leu Lys Ala
290 295 300

Thr Asn Tyr Asp Val Gln Lys Val Phe Ile Thr Gly Gln Asp Tyr Asn
305 310 315 320

Asp Thr Ala Lys Lys Leu Ile Lys Asn Gly Glu Gln Asn Met Thr Ile
325 330 335

Tyr Lys Pro Asp Val Ile Leu Gly Lys Val Ala Val Glu Val Leu Lys
340 345 350

Thr Leu Ile Asn Lys Lys Lys Ala Asn Ala Thr Ala Thr Lys Glu Asp
355 360 365

```
Val Glu Asn Ala Leu Lys Asn Asn Glu Asn Thr Lys Asp Ile His Phe
    370                 375                 380

Arg Tyr Asp Asp Thr Thr Tyr Lys Ala Gly Ser Val Gly Ala Tyr Lys
385                 390                 395                 400

Asn Ile Lys Ala Ile Leu Val Asn Pro Val Val Val Thr Lys Gln Asn
                405                 410                 415

Val Asp Asn Pro Leu Ala Asn Ala Gln Gln Ser Thr Ser Ala Asn Val
            420                 425                 430

Ser Val Ser Ala Ser Gly Thr Val Pro Thr Asn Gly Val Thr Gln
        435                 440                 445


<210> SEQ ID NO 2
<211> LENGTH: 597
<212> TYPE: PRT
<213> ORGANISM: Mycoplasma hyorhinis

<400> SEQUENCE: 2

Met Ala Lys Glu Ile Ile Leu Gly Ile Asp Leu Gly Thr Thr Asn Ser
1               5                   10                  15

Val Val Ser Ile Ile Glu Asn Gly Lys Pro Val Val Leu Glu Asn Pro
            20                  25                  30

Asn Gly Lys Asn Thr Thr Pro Ser Val Val Ala Phe Lys Asn Gly Glu
        35                  40                  45

Glu Ile Val Gly Asp Ala Ala Lys Arg Gln Leu Glu Thr Asn Pro Asp
    50                  55                  60

Ala Ile Ala Ser Ile Lys Arg Leu Met Gly Thr Asp Lys Thr Val Lys
65                  70                  75                  80

Ala Asn Gly Lys Asp Tyr Lys Pro Glu Glu Ile Ser Ala Lys Ile Leu
                85                  90                  95

Ser Tyr Leu Lys Gln Tyr Ala Glu Lys Lys Ile Gly Asn Lys Val Ser
            100                 105                 110

Lys Ala Val Ile Thr Val Pro Ala Tyr Phe Asn Asn Ala Gln Arg Glu
        115                 120                 125

Ala Thr Lys Asn Ala Gly Lys Ile Ala Gly Leu Glu Val Glu Arg Ile
    130                 135                 140

Ile Asn Glu Pro Thr Ala Ala Ala Leu Ala Phe Gly Leu Glu Lys Thr
145                 150                 155                 160

Glu Lys Glu Met Lys Val Leu Val Tyr Asp Leu Gly Gly Gly Thr Phe
                165                 170                 175

Asp Val Ser Val Leu Glu Leu Ser Gly Gly Thr Phe Glu Val Leu Ser
            180                 185                 190

Thr Ser Gly Asp Asn Lys Leu Gly Gly Asp Asp Cys Asp His Val Ile
        195                 200                 205

Val Asp Trp Leu Val Asp Lys Ile Lys Lys Glu Tyr Glu Phe Asp Pro
    210                 215                 220

Ser Lys Asp Lys Met Ala Leu Ser Arg Leu Lys Glu Glu Ala Glu Lys
225                 230                 235                 240

Thr Lys Ile Ser Leu Ser Asn Gln Ser Val Ala Thr Ile Ser Leu Pro
                245                 250                 255

Phe Leu Gly Ile Gly Pro Lys Gly Pro Ile Asn Val Glu Leu Glu Leu
            260                 265                 270

Lys Arg Ser Glu Phe Glu Lys Met Thr Ala His Leu Val Asp Lys Thr
        275                 280                 285

Arg Lys Pro Ile Met Asp Ala Leu Lys Glu Ala Lys Leu Glu Ala Lys
    290                 295                 300
```

```
Asp Leu Asp Glu Val Leu Leu Val Gly Gly Ser Thr Arg Ile Pro Ala
305                 310                 315                 320

Val Gln Thr Met Ile Glu His Thr Leu Gly Lys Lys Pro Asn Arg Ser
                325                 330                 335

Ile Asn Pro Asp Glu Val Val Ala Ile Gly Ala Ala Ile Gln Gly Gly
            340                 345                 350

Val Leu Ala Gly Glu Ile Asn Asp Val Leu Leu Leu Asp Val Thr Pro
        355                 360                 365

Leu Thr Leu Gly Ile Glu Thr Leu Gly Gly Ile Ala Thr Pro Leu Ile
    370                 375                 380

Pro Arg Asn Thr Thr Ile Pro Val Thr Lys Ser Gln Ile Phe Ser Thr
385                 390                 395                 400

Ala Glu Asn Asn Gln Thr Glu Val Thr Ile Ser Val Val Gln Gly Glu
                405                 410                 415

Arg Gln Leu Ala Ala Asp Asn Lys Leu Leu Gly Arg Phe Asn Leu Ser
            420                 425                 430

Gly Ile Glu Gln Ala Pro Arg Gly Val Pro Gln Ile Glu Val Ser Phe
        435                 440                 445

Ser Ile Asp Val Asn Gly Ile Thr Thr Val Ser Ala Lys Asp Lys Lys
    450                 455                 460

Thr Asn Lys Glu Gln Thr Ile Thr Ile Lys Asn Thr Thr Ser Leu Ser
465                 470                 475                 480

Glu Glu Glu Ile Glu Arg Met Val Lys Glu Ala Glu Glu Asn Arg Glu
                485                 490                 495

Ala Asp Ala Lys Lys Lys Glu Lys Ile Glu Val Thr Val Arg Ala Glu
            500                 505                 510

Ala Leu Ile Asn Gln Leu Glu Lys Ser Leu Glu Asp Gln Gly Asp Lys
        515                 520                 525

Val Asp Ala Lys Gln Lys Glu Thr Leu Glu Lys Gln Ile Gln Glu Leu
    530                 535                 540

Lys Asp Leu Val Lys Glu Glu Lys Ile Glu Glu Leu Lys Thr Lys Leu
545                 550                 555                 560

Asp Gln Ile Glu Gln Ala Ala Gln Ala Phe Ala Gln Ala Ala Ala Gln
                565                 570                 575

Gln Ala Asn Thr Ser Asp Thr Ser Ser Asp Asp Gln Pro Ile Glu Ala
            580                 585                 590

Glu Val Lys Glu Asn
        595


<210> SEQ ID NO 3
<211> LENGTH: 511
<212> TYPE: PRT
<213> ORGANISM: Mycoplasma hyorhinis

<400> SEQUENCE: 3

Met Asn Lys Lys His Ile Lys Thr Leu Ile Ser Ser Val Ser Ile Leu
1               5                   10                  15

Thr Pro Val Ala Ile Leu Ala Ser Cys Gly Gln Pro Thr Thr Ile Lys
            20                  25                  30

Phe Ala Thr Ser Gln Gly Ser Tyr Trp Pro Met Met Leu Gly Met Lys
        35                  40                  45

Glu Ile Ile Lys Ile Tyr Asn Glu Gln His Lys Asn Asp Ala Asp Phe
    50                  55                  60

Ile Pro Val Glu Leu Leu Thr Ser Asp Val Thr His Lys Asn Ser Glu
```

```
65                  70                  75                  80

Gly Gln Leu Leu Ser Ser Leu Asp Ser Asp Leu Ser Thr Lys Gln Ser
                85                  90                  95

Ser Asp Trp Asn Leu Ile Leu Gly Asn Lys Ala Thr Ala Tyr Val Ala
            100                 105                 110

Asn Ser Tyr Asp Lys Leu Leu Asp Val Gly Thr Ser Thr Val Asn Pro
        115                 120                 125

Asn Ser Phe Pro Thr Lys Ile Ile Asn Asn Tyr Asn Lys Leu Leu Gly
    130                 135                 140

Val Glu Gly Gln Thr Thr Leu Lys Ser Leu Pro Tyr Asn Ile Asn Asp
145                 150                 155                 160

Thr Asp Gly Ile Val Phe Asn Leu Asp Ile Met Lys Val Leu Phe Asp
                165                 170                 175

Ile Ile Lys Gln Gly Gly Gly Thr Ile Asp Glu Asn Ser Ile Ile Ala
            180                 185                 190

Lys Lys Val Lys Glu Ala Glu Gly Lys Gly Asn His Ile Pro Ser Ser
        195                 200                 205

Ser Met Phe Ser Ala Ile Lys Ile Lys Glu Ser Ser Lys Asn Thr Gly
    210                 215                 220

Phe Ser Gly Tyr Thr Val Asn Asp Ser Thr Phe Ser Asp Ile Lys Lys
225                 230                 235                 240

Ala Phe Glu Phe Ala Gln Lys Ile Tyr Asp Asn Thr Glu Ile Asp Thr
                245                 250                 255

Thr Lys Leu Ser Lys Asp Val Lys Asp Ser Glu Ile Phe Ala Ile Asp
            260                 265                 270

Tyr Ala Ser Asp Val Phe Arg Lys Glu Ile Leu Ser Lys Thr Asn Lys
        275                 280                 285

Thr Phe Trp Ser Glu Lys Ser Leu Gln Asn Asn Lys Ile Thr Leu Asp
    290                 295                 300

Val Asn Leu Asn Thr Asn Gln Ala Leu Lys Thr Glu Val Glu Asn Gln
305                 310                 315                 320

Tyr Gln Glu Trp Glu Asn Thr Leu Lys Gln Thr Gln Phe Ile Pro Thr
                325                 330                 335

Thr Thr Thr Gln Ala Asn Thr Glu Thr Thr Ser Trp Thr Lys Lys Asp
            340                 345                 350

Ile Gln Thr Lys Ser Ala Thr Asp Asp Ser Gln Gln Ser Ile Asn Ser
        355                 360                 365

Lys Thr Phe Tyr Ser Val Lys Phe Thr Glu Tyr Phe Lys Pro Ile Asn
    370                 375                 380

Gln Trp Gly Ser Phe Glu Ile Arg Gln Tyr Leu Thr Ala Phe Thr Tyr
385                 390                 395                 400

Ala Pro Leu Val Gly Thr Asn Tyr Ser Val Asp Ser Pro Trp Ser Arg
                405                 410                 415

Ala Phe Phe Lys Lys Asp Leu Glu Glu Gly Lys Gln Lys Ala Ser Glu
            420                 425                 430

Trp Thr Thr Arg Glu Asp Val Tyr Ala Thr Asn Gln Ala Met Lys Ala
        435                 440                 445

Asp Asp Asn Ala Gln Tyr Leu Ala Tyr Asn Ala Gly Gly Phe Ser Leu
    450                 455                 460

Ile Ala Ile Lys Ser Asn Ser Asp Ile Ile Asn Lys Asn Ile Ile Lys
465                 470                 475                 480

Phe Val Asp Phe Leu Tyr Asn Gly Thr Gly Leu Thr Asp Leu Thr Gly
                485                 490                 495
```

```
Ala Lys Ile Ser Ala Ala Asp Phe Met Ala Glu Lys Ser Ala Ala
            500                 505                 510

<210> SEQ ID NO 4
<211> LENGTH: 1344
<212> TYPE: DNA
<213> ORGANISM: Artificial Sequence
<220> FEATURE:
<223> OTHER INFORMATION: antigen

<400> SEQUENCE: 4

atgaaaaagt taattactaa aaaattttta tatttatcaa caatttcaac agcttcattt     60

atagcttttg cttcatttgt agcttgtgga acaacagcaa caggtttatc acaaacaaaa    120

gatcatgctg ttactaatga atccattaga gttgcattaa cagatccaga taatccaaga    180

tggattaatg cacaaaaaga tatattaaat tatatagaca aaacagaagg tgcaatttct    240

actattacta aagaccaaaa tgcacaaaac aactggttaa ctcaacaagc aaacttaaat    300

ccagcaccta aaggatttat tattgctcct gaaaatggag gaggagttgg aaccgctgtt    360

aattcaatag ctgaaaaaaa tattcctatc gttgcttatg atagattaat tactggttca    420

acttcatatg attggtatgt ttcttacgat aatgaaaaag tgggtgaact acaaggtctt    480

tcattagcag ctggattatt aggaaaaact gatggtgcat ttaaagatga aactgaaatg    540

ttaaactatc taaaagatca catgccacaa gaaactgttt cattttatgc agtagctgga    600

tcacaagatg acaacaattc tcaatacttt tacaacggag caatgaaaat tttaaaaaaa    660

ttaatggaaa actccaatgg taaagtagta gatttgtctc caagaggtaa tgcagtttat    720

gttccaggat ggaattacgg agacgctgga caaagaattc aacaattctt cacacaatat    780

cgtgattcat cagtgccaaa tggagtatta ccagttacat atgataatgt aactatccct    840

aaatctgttt taaaaggatt tttagcacca aatgatggaa tggcagaaca agcagtagac    900

aaactaaaag ctactaatta tgatgtacaa aaagttttca ttactggtca agactacaat    960

gatacagcaa aaaaacttat taaaaatggt gaacaaaata tgaccatcta caaaccagat   1020

gtaattttag gtaaagtagc tgtagaagta ttaaaaacat taataaacaa aaagaaagca   1080

aatgcaacag caactaaaga agatgttgaa aatgctttaa aaaacaacga aaatacaaaa   1140

gatattcact ttagatatga tgatacaaca tataaagctg gttcagtagg tgcttacaaa   1200

aacattaaag caattttagt taatccagtt gtagtaacta aacaaaatgt agataaccca   1260

ttagctaatg cacaacaatc tacaagtgca aatgtttctg tttctgcatc aggtacagta   1320

ccaactaatg gtgtaacaca ataa                                          1344

<210> SEQ ID NO 5
<211> LENGTH: 1794
<212> TYPE: DNA
<213> ORGANISM: Artificial Sequence
<220> FEATURE:
<223> OTHER INFORMATION: antigen

<400> SEQUENCE: 5

atggcaaaag aaattatttt aggaatagat ttaggaacaa caaattctgt tgtttctata     60

atagaaaatg gtaagccagt tgtattagaa aatccaaatg gaaaaaatac aacaccttct    120

gttgttgctt ttaaaaacgg agaagaaatc gtaggagatg ctgctaaaag acaattagaa    180

acaaatcctg acgcaattgc ttcaattaaa agattaatgg gaacagataa aacagtaaaa    240

gcaaatggaa aagactataa accagaagaa atttctgcaa aaattctttc ttatttaaaa    300
```

```
caatatgcag agaaaaaaat tggtaacaaa gtttcaaaag cagttattac tgttccagct    360
tacttcaata atgcacaaag agaagcaaca aaaaatgcag gaaaaattgc tggcttagaa    420
gtagaaagaa ttattaatga accaactgca gctgctttag cttttggact agaaaaaact    480
gaaaaagaaa tgaaagtatt agtttacgac ttaggtggag gaacatttga cgtttctgta    540
ttagaacttt caggtggaac tttcgaagtt ttatcaacta gtggagataa caaattagga    600
ggagatgact gtgatcatgt tattgttgat tggttagttg acaaaattaa aaaagaatat    660
gaatttgatc cttctaaaga caaaatggct ttatctcgtt taaaagaaga agcagaaaaa    720
acaaaaattt ctttatccaa ccaatcagtt gctacaattt cattaccatt tttgggtatt    780
ggaccaaaag gacctattaa tgttgagtta gaactaaaaa gatcagaatt tgaaaaaatg    840
acagctcatt tagtagataa aacaagaaaa ccaattatgg atgctttaaa agaagcaaaa    900
ttagaagcaa aagatttaga tgaagtttta ttagttggtg gatcaacaag aattcctgct    960
gttcaaacaa tgattgagca cacattaggt aaaaaaccaa atagatccat taatccagat   1020
gaagttgttg ctattggagc tgcaattcaa ggtggtgttt tagctggaga aattaatgat   1080
gttttattac ttgacgttac acctttaact ttaggtattg aaacattagg tggaattgct   1140
actccattaa ttccaagaaa cacaacaatt cctgttacta aatcacaaat tttctcaact   1200
gctgaaaata accaaacaga agttacaatt tcagttgttc aaggagaaag acaattagct   1260
gctgataata aattattagg tagatttaat ctctcaggaa ttgaacaagc acctagagga   1320
gttcctcaaa ttgaagttag tttctcaatt gatgttaacg gaataacaac tgtatcagca   1380
aaagataaaa aaacaaacaa agaacaaact attactatta aaaatacaac cagcttatct   1440
gaagaagaaa ttgaaagaat ggtaaaagaa gctgaagaaa atcgtgaagc agatgctaag   1500
aaaaaagaaa aaattgaagt aacagttaga gctgaagctt taattaatca attagaaaaa   1560
tctctagaag accaaggtga taaagtagat gctaaacaaa aagaaacttt agaaaaacaa   1620
attcaagaat taaaagactt ggtaaaagaa gaaaaaattg aagaattaaa aacaaaatta   1680
gaccaaattg aacaagctgc acaagctttt gctcaagctg cagcacaaca agcaaatact   1740
tctgatactt cttcagatga tcaaccaatt gaagctgaag ttaaagaaaa ttaa         1794
```

<210> SEQ ID NO 6
<211> LENGTH: 1536
<212> TYPE: DNA
<213> ORGANISM: Artificial Sequence
<220> FEATURE:
<223> OTHER INFORMATION: antigen

<400> SEQUENCE: 6

```
atgaataaaa aacatataaa aacacttatt tcaagtgtaa gtattttaac tcctgttgcc     60
attttagctt cttgtggaca accaaccaca attaaatttg ctacttctca aggttcatat    120
tggccaatga tgctaggaat gaaagaaatt attaagattt ataatgaaca acacaaaaac    180
gatgctgatt tcattcctgt tgaactttta acatcagatg taactcataa aaatagtgaa    240
ggtcaacttt taagtagttt agatagtgat ttatctacta agcaaagctc tgattggaat    300
cttattttag gaaacaaagc tactgcttat gttgcaaatt cttatgataa attattagac    360
gttggtactt ctacagtaaa tcccaattca ttccctacaa aaataattaa taattacaat    420
aaattattag gtgttgaagg acaaacaaca ttaaaaagtt taccttacaa catcaacgat    480
acagatggta ttgtttttaa tttagacatc atgaaagttc tttttgatat cataaaacaa    540
```

```
ggtggcggaa ctattgatga aaactcaata attgctaaaa aagtaaaaga agcagaagga    600
aaaggtaatc atattccatc aagttcaatg ttttctgcaa ttaaaattaa agagtcttca    660
aaaaacactg gattttctgg atatacagta aatgattcta cttttagtga tattaaaaaa    720
gcttttgagt ttgctcaaaa aatttatgat aacacagaaa ttgatacgac caaattatca    780
aaagatgtaa aagattcaga gatttttgca atagattatg cttcagatgt ttttagaaaa    840
gaaattcttt ctaaaactaa taaaactttt tggagtgaaa aaagtttaca aaataacaaa    900
attacattag atgtaaatct caatacaaat caagctctaa aaacagaagt tgaaaaccaa    960
tatcaagaat gggaaaacac tttaaaacaa acacaattta taccaactac aacaactcaa   1020
gcaaatactg aaactacttc atggacaaaa aaagatattc aaactaaatc agcaactgat   1080
gatagtcaac aatccattaa ttctaaaaca ttttattctg ttaaatttac tgaatacttt   1140
aaacctataa atcaatgggg atcttttgaa attagacaat atttaactgc atttacttat   1200
gctcctctag taggaacaaa ctattctgta gattctcctt ggtcacgtgc attttttaaa   1260
aaagatttag aagaaggaaa acaaaaagct tcagaatgga caacaagaga agatgtttat   1320
gctacaaatc aagcaatgaa agcagatgat aatgcacaat atttagcata taacgctggt   1380
ggtttttctt taattgctat caaatccaac agtgatataa taaataaaaa tatcattaaa   1440
tttgtagact ttttatacaa tggaacagga ctaacagatt taactggtgc taaaatttca   1500
gctgctgatt ttatggccga aaaatctgca gcttaa                             1536
```

<210> SEQ ID NO 7
<211> LENGTH: 7245
<212> TYPE: DNA
<213> ORGANISM: Artificial Sequence
<220> FEATURE:
<223> OTHER INFORMATION: vector

<400> SEQUENCE: 7

```
atccggatat agttcctcct ttcagcaaaa aacccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttgt    180
cgacttgtgt tacaccatta gttggtactg tacctgatgc agaaacagaa acatttgcac    240
ttgtagattg ttgtgcatta gctaatgggt tatctacatt ttgtttagtt actacaactg    300
gattaactaa aattgcttta atgtttttgt aagcacctac tgaaccagct ttatatgttg    360
tatcatcata tctaaagtga atatcttttg tattttcgtt gtttttaaa gcattttcaa    420
catcttcttt agttgctgtt gcatttgctt tctttttgtt tattaatgtt tttaatactt    480
ctacagctac tttacctaaa attacatctg gtttgtagat ggtcatattt tgttcaccat    540
ttttaataag tttttttgct gtatcattgt agtcttgacc agtaatgaaa actttttgta    600
catcataatt agtagctttt agtttgtcta ctgcttgttc tgccattcca tcatttggtg    660
ctaaaaatcc ttttaaaaca gatttaggga tagttacatt atcatatgta actggtaata    720
ctccatttgg cactgatgaa tcacgatatt gtgtgaagaa ttgttgaatt ctttgtccag    780
cgtctccgta attccatcct ggaacataaa ctgcattacc tcttggagac aaatctacta    840
ctttaccatt ggagttttcc attaattttt ttaaaatttt cattgctccg ttgtaaaagt    900
attgagaatt gttgtcatct tgtgatccag ctactgcata aaatgaaaca gtttcttgtg    960
gcatgtgatc ttttagatag tttaacattt cagtttcatc tttaaatgca ccatcagttt   1020
ttcctaataa tccagctgct aatgaaagac cttgtagttc acccactttt tcattatcgt   1080
```

```
aagaaacata ccaatcatat gaagttgaac cagtaattaa tctatcataa gcaacgatag   1140
gaatattttt ttcagctatt gaattaacag cggttccaac tcctcctcca ttttcaggag   1200
caataataaa tcctttaggt gctggattta agtttgcttg ttgagttaac cagttgtttt   1260
gtgcattttg gtctttagta atagtagaaa ttgcaccttc tgttttgtct atataattta   1320
atatatcttt ttgtgcatta atccatcttg gattatctgg atctgttaat gcaactctaa   1380
tggattcatt agtaacagca tgatcttttg tttgtgataa acctgttgct gttgttccac   1440
aagctacaaa tgaggatcct ttaccgctgg tcattttttg gtgttcgtcg aggaattctt   1500
tcatctcttt cggcggctgg taacccggaa caagtgtgcc attgctcagc acaactgccg   1560
gagtaccgct aacgccaagc tggacgccaa gtgcgtaatg gtcggcaata tccacgtcgc   1620
aactggctgg tgcgacgctt ttacctgcca tcacatcatc aaacgctttg tttttatctt   1680
tcgcacacca gatagctttc atttctttct ctgcatcgct gtccagcccc tggcgcggga   1740
aagcaagata acgcacggtg atccccagcg cgttgtagtc tgccatttgc tcatgcagtt   1800
tgtggcagta accacaggta atatcagtaa acacggtgat gacgtgtttt tcctgcggcg   1860
ctttataaac gatcatctct tttcaagcg cattcaactg ctttaacagc atcttattgg   1920
tgacattgac cggagccgtg ccactaacgt catacattgg cccctgaatg atatgtttac   1980
catcatcggt gatgtacaac acgccgctgt tagtcagaac tgtcttcatg ccagctacag   2040
gcgcgggctg aatatcgctg cttttgatgc ccattttggc taacgtttgt tgaattgccg   2100
cgtcatcggt acccagatct gggctgtcca tgtgctggcg ttcgaattta gcagcagcgg   2160
tttctttcat atgtatatct ccttcttaaa gttaaacaaa attatttcta gaggggaatt   2220
gttatccgct cacaattccc ctatagtgag tcgtattaat ttcgcgggat cgagatcgat   2280
ctcgatcctc tacgccggac gcatcgtggc cggcatcacc ggcgccacag gtgcggttgc   2340
tggcgcctat atcgccgaca tcaccgatgg ggaagatcgg gctcgccact tcgggctcat   2400
gagcgcttgt ttcggcgtgg gtatggtggc aggccccgtg gccgggggac tgttgggcgc   2460
catctccttg catgcaccat tccttgcggc ggcggtgctc aacggcctca acctactact   2520
gggctgcttc ctaatgcagg agtcgcataa gggagagcgt cgagatcccg gacaccatcg   2580
aatggcgcaa aacctttcgc ggtatggcat gatagcgccc ggaagagagt caattcaggg   2640
tggtgaatgt gaaaccagta acgttatacg atgtcgcaga gtatgccggt gtctcttatc   2700
agaccgtttc ccgcgtggtg aaccaggcca gccacgtttc tgcgaaaacg cgggaaaaag   2760
tggaagcggc gatggcggag ctgaattaca ttcccaaccg cgtggcacaa caactggcgg   2820
gcaaacagtc gttgctgatt ggcgttgcca cctccagtct ggccctgcac gcgccgtcgc   2880
aaattgtcgc ggcgattaaa tctcgcgccg atcaactggg tgccagcgtg gtggtgtcga   2940
tggtagaacg aagcggcgtc gaagcctgta aagcggcggt gcacaatctt ctcgcgcaac   3000
gcgtcagtgg gctgatcatt aactatccgc tggatgacca ggatgccatt gctgtggaag   3060
ctgcctgcac taatgttccg gcgttatttc ttgatgtctc tgaccagaca cccatcaaca   3120
gtattatttt ctcccatgaa gacggtacgc gactgggcgt ggagcatctg gtcgcattgg   3180
gtcaccagca aatcgcgctg ttagcgggcc cattaagttc tgtctcggcg cgtctgcgtc   3240
tggctggctg gcataaatat ctcactcgca atcaaattca gccgatagcg gaacgggaag   3300
gcgactggag tgccatgtcc ggttttcaac aaaccatgca aatgctgaat gagggcatcg   3360
ttcccactgc gatgctggtt gccaacgatc agatggcgct gggcgcaatg cgcgccatta   3420
```

```
ccgagtccgg gctgcgcgtt ggtgcggaca tctcggtagt gggatacgac gataccgaag   3480
acagctcatg ttatatcccg ccgttaacca ccatcaaaca ggattttcgc ctgctggggc   3540
aaaccagcgt ggaccgcttg ctgcaactct ctcagggcca ggcggtgaag ggcaatcagc   3600
tgttgcccgt ctcactggtg aaaagaaaaa ccaccctggc gcccaatacg caaaccgcct   3660
ctccccgcgc gttggccgat tcattaatgc agctggcacg acaggtttcc cgactggaaa   3720
gcgggcagtg agcgcaacgc aattaatgta agttagctca ctcattaggc accgggatct   3780
cgaccgatgc ccttgagagc cttcaaccca gtcagctcct tccggtgggc gcggggcatg   3840
actatcgtcg ccgcacttat gactgtcttc tttatcatgc aactcgtagg acaggtgccg   3900
gcagcgctct gggtcatttt cggcgaggac cgctttcgct ggagcgcgac gatgatcggc   3960
ctgtcgcttg cggtattcgg aatcttgcac gccctcgctc aagccttcgt cactggtccc   4020
gccaccaaac gtttcggcga gaagcaggcc attatcgccg gcatggcggc cccacgggtg   4080
cgcatgatcg tgctcctgtc gttgaggacc cggctaggct ggcggggttg ccttactggt   4140
tagcagaatg aatcaccgat acgcgagcga acgtgaagcg actgctgctg caaaacgtct   4200
gcgacctgag caacaacatg aatggtcttc ggtttccgtg tttcgtaaag tctggaaacg   4260
cggaagtcag cgccctgcac cattatgttc cggatctgca tcgcaggatg ctgctggcta   4320
ccctgtggaa cacctacatc tgtattaacg aagcgctggc attgaccctg agtgattttt   4380
ctctggtccc gccgcatcca taccgccagt tgtttaccct cacaacgttc cagtaaccgg   4440
gcatgttcat catcagtaac ccgtatcgtg agcatcctct ctcgtttcat cggtatcatt   4500
acccccatga acagaaatcc cccttacacg gaggcatcag tgaccaaaca ggaaaaaacc   4560
gcccttaaca tggcccgctt tatcagaagc cagacattaa cgcttctgga gaaactcaac   4620
gagctggacg cggatgaaca ggcagacatc tgtgaatcgc ttcacgacca cgctgatgag   4680
ctttaccgca gctgcctcgc gcgtttcggt gatgacggtg aaaacctctg acacatgcag   4740
ctcccggaga cggtcacagc ttgtctgtaa gcggatgccg ggagcagaca agcccgtcag   4800
ggcgcgtcag cgggtgttgg cgggtgtcgg ggcgcagcca tgacccagtc acgtagcgat   4860
agcggagtgt atactggctt aactatgcgg catcagagca gattgtactg agagtgcacc   4920
atatatgcgg tgtgaaatac cgcacagatg cgtaaggaga aaataccgca tcaggcgctc   4980
ttccgcttcc tcgctcactg actcgctgcg ctcggtcgtt cggctgcggc gagcggtatc   5040
agctcactca aaggcggtaa tacggttatc cacagaatca ggggataacg caggaaagaa   5100
catgtgagca aaaggccagc aaaaggccag gaaccgtaaa aaggccgcgt tgctggcgtt   5160
tttccatagg ctccgccccc ctgacgagca tcacaaaaat cgacgctcaa gtcagaggtg   5220
gcgaaacccg acaggactat aaagatacca ggcgtttccc cctggaagct ccctcgtgcg   5280
ctctcctgtt ccgaccctgc cgcttaccgg atacctgtcc gcctttctcc cttcgggaag   5340
cgtggcgctt tctcatagct cacgctgtag gtatctcagt tcggtgtagg tcgttcgctc   5400
caagctgggc tgtgtgcacg aaccccccgt tcagcccgac cgctgcgcct tatccggtaa   5460
ctatcgtctt gagtccaacc cggtaagaca cgacttatcg ccactggcag cagccactgg   5520
taacaggatt agcagagcga ggtatgtagg cggtgctaca gagttcttga agtggtggcc   5580
taactacggc tacactagaa ggacagtatt tggtatctgc gctctgctga agccagttac   5640
cttcggaaaa agagttggta gctcttgatc cggcaaacaa accaccgctg gtagcggtgg   5700
tttttttgtt tgcaagcagc agattacgcg cagaaaaaaa ggatctcaag aagatccttt   5760
gatcttttct acggggtctg acgctcagtg gaacgaaaac tcacgttaag ggattttggt   5820
```

```
catgaacaat aaaactgtct gcttacataa acagtaatac aaggggtgtt atgagccata   5880

ttcaacggga aacgtcttgc tctaggccgc gattaaattc caacatggat gctgatttat   5940

atgggtataa atgggctcgc gataatgtcg ggcaatcagg tgcgacaatc tatcgattgt   6000

atgggaagcc cgatgcgcca gagttgtttc tgaaacatgg caaaggtagc gttgccaatg   6060

atgttacaga tgagatggtc agactaaact ggctgacgga atttatgcct cttccgacca   6120

tcaagcattt tatccgtact cctgatgatg catggttact caccactgcg atccccggga   6180

aaacagcatt ccaggtatta gaagaatatc ctgattcagg tgaaaatatt gttgatgcgc   6240

tggcagtgtt cctgcgccgg ttgcattcga ttcctgtttg taattgtcct tttaacagcg   6300

atcgcgtatt tcgtctcgct caggcgcaat cacgaatgaa taacggtttg gttgatgcga   6360

gtgattttga tgacgagcgt aatggctggc ctgttgaaca agtctggaaa gaaatgcata   6420

aacttttgcc attctcaccg gattcagtcg tcactcatgg tgatttctca cttgataacc   6480

ttatttttga cgaggggaaa ttaataggtt gtattgatgt tggacgagtc ggaatcgcag   6540

accgatacca ggatcttgcc atcctatgga actgcctcgg tgagttttct ccttcattac   6600

agaaacggct ttttcaaaaa tatggtattg ataatcctga tatgaataaa ttgcagtttc   6660

atttgatgct cgatgagttt ttctaagaat taattcatga gcggatacat atttgaatgt   6720

atttagaaaa ataaacaaat aggggttccg cgcacatttc cccgaaaagt gccacctgaa   6780

attgtaaacg ttaatatttt gttaaaattc gcgttaaatt tttgttaaat cagctcattt   6840

tttaaccaat aggccgaaat cggcaaaatc ccttataaat caaaagaata gaccgagata   6900

gggttgagtg ttgttccagt ttggaacaag agtccactat taaagaacgt ggactccaac   6960

gtcaaagggc gaaaaaccgt ctatcagggc gatggcccac tacgtgaacc atcaccctaa   7020

tcaagttttt tggggtcgag gtgccgtaaa gcactaaatc ggaaccctaa agggagcccc   7080

cgatttagag cttgacgggg aaagccggcg aacgtggcga gaaaggaagg gaagaaagcg   7140

aaaggagcgg gcgctagggc gctggcaagt gtagcggtca cgctgcgcgt aaccaccaca   7200

cccgccgcgc ttaatgcgcc gctacagggc gcgtcccatt cgcca                   7245
```

<210> SEQ ID NO 8
<211> LENGTH: 7500
<212> TYPE: DNA
<213> ORGANISM: Artificial Sequence
<220> FEATURE:
<223> OTHER INFORMATION: vector

<400> SEQUENCE: 8

```
atccggatat agttcctcct ttcagcaaaa aacccctcaa gacccgttta gaggccccaa     60

ggggttatgc tagttattgc tcagcggtgg cagcagccaa ctcagcttcc tttcgggctt    120

tgttagcagc cggatctcag tggtggtggt ggtggtgctc gagtgcggcc gcaagcttgt    180

cgacttaatt ttctttaact tcagcttcaa ttggttgatc atctgaagaa gtatcagaag    240

tatttgcttg ttgtgctgca gcttgagcaa aagcttgtgc agcttgttca atttggtcta    300

attttgtttt taattcttca attttttctt cttttaccaa gtcttttaat tcttgaattt    360

gtttttctaa agtttctttt tgtttagcat ctactttatc accttggtct tctagagatt    420

tttctaattg attaattaaa gcttcagctc taactgttac ttcaattttt tctttttttct    480

tagcatctgc ttcacgattt tcttcagctt cttttaccat tctttcaatt tcttcttcag    540

ataagctggt tgtattttta atagtaatag tttgttcttt gtttgttttt ttatcttttg    600
```

-continued ctgatacagt tgttattccg ttaacatcaa ttgagaaact aacttcaatt tgaggaactc 660
ctctaggtgc ttgttcaatt cctgagagat taaatctacc taataattta ttatcagcag 720
ctaattgtct ttctccttga acaactgaaa ttgtaacttc tgtttggtta ttttcagcag 780
ttgagaaaat ttgtgattta gtaacaggaa ttgttgtgtt tcttggaatt aatggagtag 840
caattccacc taatgtttca atacctaaag ttaaaggtgt aacgtcaagt aataaaacat 900
cattaatttc tccagctaaa acaccacctt gaattgcagc tccaatagca acaacttcat 960
ctggattaat ggatctattt ggttttttac ctaatgtgtg ctcaatcatt gtttgaacag 1020
caggaattct tgttgatcca ccaactaata aaacttcatc taaatctttt gcttctaatt 1080
ttgcttcttt taaagcatcc ataattggtt ttcttgtttt atctactaaa tgagctgtca 1140 tttttcaaa ttctgatctt tttagttcta actcaacatt aataggtcct tttggtccaa 1200
tacccaaaaa tggtaatgaa attgtagcaa ctgattggtt ggataaagaa atttttgttt 1260
tttctgcttc ttcttttaaa cgagataaag ccattttgtc tttagaagga tcaaattcat 1320
attctttttt aattttgtca actaaccaat caacaataac atgatcacag tcatctcctc 1380
ctaatttgtt atctccacta gttgataaaa cttcgaaagt tccacctgaa agttctaata 1440
cagaaacgtc aaatgttcct ccacctaagt cgtaaactaa tactttcatt tctttttcag 1500
ttttttctag tccaaaagct aaagcagctg cagttggttc attaataatt ctttctactt 1560
ctaagccagc aatttttcct gcattttttg ttgcttctct ttgtgcatta ttgaagtaag 1620
ctggaacagt aataactgct tttgaaactt tgttaccaat ttttttctct gcatattgtt 1680
ttaaataaga aagaattttt gcagaaattt cttctggttt atagtctttt ccatttgctt 1740
ttactgtttt atctgttccc attaatcttt taattgaagc aattgcgtca ggatttgttt 1800
ctaattgtct tttagcagca tctcctacga tttcttctcc gtttttaaaa gcaacaacag 1860
aaggtgttgt attttttcca tttggatttt ctaatacaac tggcttacca ttttctatta 1920
tagaaacaac agaatttgtt gttcctaaat ctattcctaa aataatttct tttgccatgg 1980
atccggtgcc gccaccagaa cgttcatccc actcatcagc tgctgcgcgt ccttcctcgg 2040
tatccagcgg tggctcaagc tgaaattccc cctcgtccca ttcatgtaat gtattctctt 2100
cctgccactc ctggcgtatc tctatctcat catagtcgcc atcaaaaaca ctttgcgcgg 2160
cttcaccgct aagcataggt aaacattcac cttcttcccc ttcgtcggca aaaaactcaa 2220
cttgccacat gatgtcgccg tcctgcaaaa cgtatttttg ggcattgaac tgttgcacat 2280
tcgcatcttc ggcgtcgatg ccggggttgt ctgcaagaaa ttcttcgcgt gcagcgtcaa 2340
tggcttcttc aagcgttgcg tacatggtca tggtaccacc accgctgtga tggtgatggt 2400
gatgcgatac gaattttttt ttcatatgta tatctccttc ttaaagttaa acaaaattat 2460
ttctagaggg gaattgttat ccgctcacaa ttcccctata gtgagtcgta ttaatttcgc 2520
gggatcgaga tcgatctcga tcctctacgc cggacgcatc gtggccggca tcaccggcgc 2580
cacaggtgcg gttgctggcg cctatatcgc cgacatcacc gatggggaag atcgggctcg 2640
ccacttcggg ctcatgagcg cttgtttcgg cgtgggtatg gtggcaggcc ccgtggccgg 2700
gggactgttg ggcgccatct ccttgcatgc accattcctt gcggcggcgg tgctcaacgg 2760
cctcaaccta ctactgggct gcttcctaat gcaggagtcg cataagggag agcgtcgaga 2820
tcccggacac catcgaatgg cgcaaaacct ttcgcggtat ggcatgatag cgcccggaag 2880
agagtcaatt cagggtggtg aatgtgaaac cagtaacgtt atacgatgtc gcagagtatg 2940
ccggtgtctc ttatcagacc gtttcccgcg tggtgaacca ggccagccac gtttctgcga 3000

```
aaacgcggga aaaagtggaa gcggcgatgg cggagctgaa ttacattccc aaccgcgtgg   3060
cacaacaact ggcgggcaaa cagtcgttgc tgattggcgt tgccacctcc agtctggccc   3120
tgcacgcgcc gtcgcaaatt gtcgcggcga ttaaatctcg cgccgatcaa ctgggtgcca   3180
gcgtggtggt gtcgatggta gaacgaagcg gcgtcgaagc ctgtaaagcg gcggtgcaca   3240
atcttctcgc gcaacgcgtc agtgggctga tcattaacta tccgctggat gaccaggatg   3300
ccattgctgt ggaagctgcc tgcactaatg ttccggcgtt atttcttgat gtctctgacc   3360
agacacccat caacagtatt attttctccc atgaagacgg tacgcgactg ggcgtggagc   3420
atctggtcgc attgggtcac cagcaaatcg cgctgttagc gggcccatta agttctgtct   3480
cggcgcgtct gcgtctggct ggctggcata aatatctcac tcgcaatcaa attcagccga   3540
tagcggaacg ggaaggcgac tggagtgcca tgtccggttt tcaacaaacc atgcaaatgc   3600
tgaatgaggg catcgttccc actgcgatgc tggttgccaa cgatcagatg gcgctgggcg   3660
caatgcgcgc cattaccgag tccgggctgc gcgttggtgc ggacatctcg gtagtgggat   3720
acgacgatac cgaagacagc tcatgttata tcccgccgtt aaccaccatc aaacaggatt   3780
ttcgcctgct ggggcaaacc agcgtggacc gcttgctgca actctctcag ggccaggcgg   3840
tgaagggcaa tcagctgttg cccgtctcac tggtgaaaag aaaaaccacc ctggcgccca   3900
atacgcaaac cgcctctccc cgcgcgttgg ccgattcatt aatgcagctg gcacgacagg   3960
tttcccgact ggaaagcggg cagtgagcgc aacgcaatta atgtaagtta gctcactcat   4020
taggcaccgg gatctcgacc gatgcccttg agagccttca acccagtcag ctccttccgg   4080
tgggcgcggg gcatgactat cgtcgccgca cttatgactg tcttctttat catgcaactc   4140
gtaggacagg tgccggcagc gctctgggtc attttcggcg aggaccgctt tcgctggagc   4200
gcgacgatga tcggcctgtc gcttgcggta ttcggaatct tgcacgccct cgctcaagcc   4260
ttcgtcactg gtcccgccac caaacgtttc ggcgagaagc aggccattat cgccggcatg   4320
gcggccccac gggtgcgcat gatcgtgctc ctgtcgttga ggacccggct aggctggcgg   4380
ggttgcctta ctggttagca gaatgaatca ccgatacgcg agcgaacgtg aagcgactgc   4440
tgctgcaaaa cgtctgcgac ctgagcaaca acatgaatgg tcttcggttt ccgtgtttcg   4500
taaagtctgg aaacgcggaa gtcagcgccc tgcaccatta tgttccggat ctgcatcgca   4560
ggatgctgct ggctaccctg tggaacacct acatctgtat taacgaagcg ctggcattga   4620
ccctgagtga tttttctctg gtcccgccgc atccataccg ccagttgttt accctcacaa   4680
cgttccagta accgggcatg ttcatcatca gtaacccgta tcgtgagcat cctctctcgt   4740
ttcatcggta tcattacccc catgaacaga aatccccctt acacggaggc atcagtgacc   4800
aaacaggaaa aaaccgccct taacatggcc cgctttatca gaagccagac attaacgctt   4860
ctggagaaac tcaacgagct ggacgcggat gaacaggcag acatctgtga atcgcttcac   4920
gaccacgctg atgagcttta ccgcagctgc ctcgcgcgtt tcggtgatga cggtgaaaac   4980
ctctgacaca tgcagctccc ggagacggtc acagcttgtc tgtaagcgga tgccgggagc   5040
agacaagccc gtcagggcgc gtcagcgggt gttggcgggt gtcggggcgc agccatgacc   5100
cagtcacgta gcgatagcgg agtgtatact ggcttaacta tgcggcatca gagcagattg   5160
tactgagagt gcaccatata tgcggtgtga aataccgcac agatgcgtaa ggagaaaata   5220
ccgcatcagg cgctcttccg cttcctcgct cactgactcg ctgcgctcgg tcgttcggct   5280
gcggcgagcg gtatcagctc actcaaaggc ggtaatacgg ttatccacag aatcagggga   5340
```

```
taacgcagga aagaacatgt gagcaaaagg ccagcaaaag gccaggaacc gtaaaaaggc   5400
cgcgttgctg gcgtttttcc ataggctccg cccccctgac gagcatcaca aaaatcgacg   5460
ctcaagtcag aggtggcgaa acccgacagg actataaaga taccaggcgt ttccccctgg   5520
aagctccctc gtgcgctctc ctgttccgac cctgccgctt accggatacc tgtccgcctt   5580
tctcccttcg ggaagcgtgg cgctttctca tagctcacgc tgtaggtatc tcagttcggt   5640
gtaggtcgtt cgctccaagc tgggctgtgt gcacgaaccc cccgttcagc ccgaccgctg   5700
cgccttatcc ggtaactatc gtcttgagtc caacccggta agacacgact tatcgccact   5760
ggcagcagcc actggtaaca ggattagcag agcgaggtat gtaggcggtg ctacagagtt   5820
cttgaagtgg tggcctaact acggctacac tagaaggaca gtatttggta tctgcgctct   5880
gctgaagcca gttaccttcg gaaaaagagt tggtagctct tgatccggca aacaaaccac   5940
cgctggtagc ggtggttttt ttgtttgcaa gcagcagatt acgcgcagaa aaaaaggatc   6000
tcaagaagat cctttgatct tttctacggg gtctgacgct cagtggaacg aaaactcacg   6060
ttaagggatt ttggtcatga acaataaaac tgtctgctta cataaacagt aatacaaggg   6120
gtgttatgag ccatattcaa cgggaaacgt cttgctctag gccgcgatta aattccaaca   6180
tggatgctga tttatatggg tataaatggg ctcgcgataa tgtcgggcaa tcaggtgcga   6240
caatctatcg attgtatggg aagcccgatg cgccagagtt gtttctgaaa catggcaaag   6300
gtagcgttgc caatgatgtt acagatgaga tggtcagact aaactggctg acggaattta   6360
tgcctcttcc gaccatcaag cattttatcc gtactcctga tgatgcatgg ttactcacca   6420
ctgcgatccc cgggaaaaca gcattccagg tattagaaga atatcctgat tcaggtgaaa   6480
atattgttga tgcgctggca gtgttcctgc gccggttgca ttcgattcct gtttgtaatt   6540
gtccttttaa cagcgatcgc gtatttcgtc tcgctcaggc gcaatcacga atgaataacg   6600
gtttggttga tgcgagtgat tttgatgacg agcgtaatgg ctggcctgtt gaacaagtct   6660
ggaaagaaat gcataaactt ttgccattct caccggattc agtcgtcact catggtgatt   6720
tctcacttga taaccttatt tttgacgagg ggaaattaat aggttgtatt gatgttggac   6780
gagtcggaat cgcagaccga taccaggatc ttgccatcct atggaactgc ctcggtgagt   6840
tttctccttc attacagaaa cggctttttc aaaaatatgg tattgataat cctgatatga   6900
ataaattgca gtttcatttg atgctcgatg agtttttcta agaattaatt catgagcgga   6960
tacatatttg aatgtattta gaaaaataaa caaatagggg ttccgcgcac atttccccga   7020
aaagtgccac ctgaaattgt aaacgttaat attttgttaa aattcgcgtt aaatttttgt   7080
taaatcagct cattttttaa ccaataggcc gaaatcggca aaatccctta taaatcaaaa   7140
gaatagaccg agatagggtt gagtgttgtt ccagtttgga acaagagtcc actattaaag   7200
aacgtggact ccaacgtcaa agggcgaaaa accgtctatc agggcgatgg cccactacgt   7260
gaaccatcac cctaatcaag ttttttgggg tcgaggtgcc gtaaagcact aaatcggaac   7320
cctaaaggga gcccccgatt tagagcttga cggggaaagc cggcgaacgt ggcgagaaag   7380
gaagggaaga aagcgaaagg agcgggcgct agggcgctgg caagtgtagc ggtcacgctg   7440
cgcgtaacca ccacacccgc cgcgcttaat gcgccgctac agggcgcgtc ccattcgcca   7500
```

<210> SEQ ID NO 9
<211> LENGTH: 7431
<212> TYPE: DNA
<213> ORGANISM: Artificial Sequence
<220> FEATURE:
<223> OTHER INFORMATION: vector

<400> SEQUENCE: 9

```
atccggatat agttcctcct ttcagcaaaa aacccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttgt    180
cgacttagtg atggtgatgg tgatgagctg cagatttttc ggccataaaa tcagcagctg    240
aaattttagc accagttaaa tctgttagtc ctgttccatt gtataaaaag tctacaaatt    300
taatgatatt tttatttatt atatcactgt tggatttgat agcaattaaa gaaaaaccac    360
cagcgttata tgctaaatat tgtgcattat catctgcttt cattgcttga tttgtagcat    420
aaacatcttc tcttgttgtc cattctgaag ctttttgttt tccttcttct aaatcttttt    480
taaaaaatgc acgtgaccaa ggagaatcta cagaatagtt tgttcctact agaggagcat    540
aagtaaatgc agttaaatat tgtctaattt caaaagatcc ccattgattt ataggtttaa    600
agtattcagt aaatttaaca gaataaaatg ttttagaatt aatggattgt tgactatcat    660
cagttgctga tttagtttga atatcttttt ttgtccatga agtagtttca gtatttgctt    720
gagttgttgt agttggtata aattgtgttt gttttaaagt gttttcccat tcttgatatt    780
ggttttcaac ttctgttttt agagcttgat ttgtattgag atttacatct aatgtaattt    840
tgttattttg taaacttttt tcactccaaa aagttttatt agttttagaa agaatttctt    900
ttctaaaaac atctgaagca taatctattg caaaaatctc tgaatctttt acatcttttg    960
ataatttggt cgtatcaatt tctgtgttat cataaatttt ttgagcaaac tcaaaagctt   1020
ttttaatatc actaaaagta gaatcattta ctgtatatcc agaaaatcca gtgtttttttg   1080
aagactcttt aattttaatt gcagaaaaca ttgaacttga tggaatatga ttaccttttc   1140
cttctgcttc ttttactttt ttagcaatta ttgagttttc atcaatagtt ccgccacctt   1200
gttttatgat atcaaaaaga actttcatga tgtctaaatt aaaaacaata ccatctgtat   1260
cgttgatgtt gtaaggtaaa ctttttaatg ttgtttgtcc ttcaacacct aataatttat   1320
tgtaattatt aattattttt gtagggaatg aattgggatt tactgtagaa gtaccaacgt   1380
ctaataattt atcataagaa tttgcaacat aagcagtagc tttgtttcct aaaataagat   1440
tccaatcaga gctttgctta gtagataaat cactatctaa actacttaaa agttgacctt   1500
cactattttt atgagttaca tctgatgtta aaagttcaac aggaatgaaa tcagcatcgt   1560
ttttgtgttg ttcattataa atcttaataa tttctttcat tcctagcatc attggccaat   1620
atgaaccttg agaagtagca aatttaattg tggttggttg tccacaagag gatccgagga   1680
tttccagcag ttcgacttca aacaccaggg tgctgaacgg agggatggat gcgcctgcgc   1740
cgcgctcgcc atatgccagt tcctgcggga tagtcagttc ccatttagaa cctaccggca   1800
tcagagtcag tgcttcaatc cagccaggga tcacgccatt aaccgggaat tcagcgggtt   1860
caccacgagc aacggagctg tcaaacacgg tgccgtcgat cagtttaccg gtgtaatgaa   1920
cacgaacgcg gtcggtacgt gccggaattg cgccttcacc ctggttgatc acgcggaatt   1980
gcaggccaga ttcggtgcta ttcacacctt cttttttggc gttttcttcc aggtatttca   2040
caccttcagc agccatcgcc tggaaacgct gacgacgaac ggcatcggcg cgctcgtgga   2100
tttcacgcag cgcgcgatgc accacatcaa ccggaacagc cggatgtttg ccttccagcg   2160
catcggcaat acctgcaacc agtgcttctg gcagcagccc ttccaggcca gattcactca   2220
gttgttgccc tacctgcaaa ccaatgccgt agcttgcttg cgcttcgatg gtgtcaaaag   2280
```

-continued

```
ttggggtggt catggtaccc agatctgggc tgtccatgtg ctggcgttcg aatttagcag   2340
cagcggtttc tttcatatgt atatctcctt cttaaagtta aacaaaatta tttctagagg   2400
ggaattgtta tccgctcaca attcccctat agtgagtcgt attaatttcg cgggatcgag   2460
atcgatctcg atcctctacg ccggacgcat cgtggccggc atcaccggcg ccacaggtgc   2520
ggttgctggc gcctatatcg ccgacatcac cgatggggaa gatcgggctc gccacttcgg   2580
gctcatgagc gcttgtttcg gcgtgggtat ggtggcaggc cccgtggccg ggggactgtt   2640
gggcgccatc tccttgcatg caccattcct tgcggcggcg gtgctcaacg gcctcaacct   2700
actactgggc tgcttcctaa tgcaggagtc gcataaggga gagcgtcgag atcccggaca   2760
ccatcgaatg gcgcaaaacc tttcgcggta tggcatgata gcgcccggaa gagagtcaat   2820
tcagggtggt gaatgtgaaa ccagtaacgt tatacgatgt cgcagagtat gccggtgtct   2880
cttatcagac cgtttcccgc gtggtgaacc aggccagcca cgtttctgcg aaaacgcggg   2940
aaaaagtgga agcggcgatg gcggagctga attacattcc caaccgcgtg gcacaacaac   3000
tggcgggcaa acagtcgttg ctgattggcg ttgccacctc cagtctggcc ctgcacgcgc   3060
cgtcgcaaat tgtcgcggcg attaaatctc gcgccgatca actgggtgcc agcgtggtgg   3120
tgtcgatggt agaacgaagc ggcgtcgaag cctgtaaagc ggcggtgcac aatcttctcg   3180
cgcaacgcgt cagtgggctg atcattaact atccgctgga tgaccaggat gccattgctg   3240
tggaagctgc ctgcactaat gttccggcgt tatttcttga tgtctctgac cagacaccca   3300
tcaacagtat tattttctcc catgaagacg gtacgcgact gggcgtggag catctggtcg   3360
cattgggtca ccagcaaatc gcgctgttag cgggcccatt aagttctgtc tcggcgcgtc   3420
tgcgtctggc tggctggcat aaatatctca ctcgcaatca aattcagccg atagcggaac   3480
gggaaggcga ctggagtgcc atgtccggtt ttcaacaaac catgcaaatg ctgaatgagg   3540
gcatcgttcc cactgcgatg ctggttgcca acgatcagat ggcgctgggc gcaatgcgcg   3600
ccattaccga gtccgggctg cgcgttggtg cggacatctc ggtagtggga tacgacgata   3660
ccgaagacag ctcatgttat atcccgccgt taaccaccat caaacaggat tttcgcctgc   3720
tggggcaaac cagcgtggac cgcttgctgc aactctctca gggccaggcg gtgaagggca   3780
atcagctgtt gcccgtctca ctggtgaaaa gaaaaaccac cctggcgccc aatacgcaaa   3840
ccgcctctcc ccgcgcgttg gccgattcat taatgcagct ggcacgacag gtttcccgac   3900
tggaaagcgg gcagtgagcg caacgcaatt aatgtaagtt agctcactca ttaggcaccg   3960
ggatctcgac cgatgccctt gagagccttc aacccagtca gctccttccg gtgggcgcgg   4020
ggcatgacta tcgtcgccgc acttatgact gtcttcttta tcatgcaact cgtaggacag   4080
gtgccggcag cgctctgggt cattttcggc gaggaccgct ttcgctggag cgcgacgatg   4140
atcggcctgt cgcttgcggt attcggaatc ttgcacgccc tcgctcaagc cttcgtcact   4200
ggtcccgcca ccaaacgttt cggcgagaag caggccatta tcgccggcat ggcggcccca   4260
cgggtgcgca tgatcgtgct cctgtcgttg aggacccggc taggctggcg gggttgcctt   4320
actggttagc agaatgaatc accgatacgc gagcgaacgt gaagcgactg ctgctgcaaa   4380
acgtctgcga cctgagcaac aacatgaatg gtcttcggtt tccgtgtttc gtaaagtctg   4440
gaaacgcgga agtcagcgcc ctgcaccatt atgttccgga tctgcatcgc aggatgctgc   4500
tggctaccct gtggaacacc tacatctgta ttaacgaagc gctggcattg accctgagtg   4560
atttttctct ggtcccgccg catccatacc gccagttgtt taccctcaca acgttccagt   4620
aaccgggcat gttcatcatc agtaacccgt atcgtgagca tcctctctcg tttcatcggt   4680
```

```
atcattaccc ccatgaacag aaatccccct tacacggagg catcagtgac caaacaggaa   4740
aaaaccgccc ttaacatggc ccgctttatc agaagccaga cattaacgct tctggagaaa   4800
ctcaacgagc tggacgcgga tgaacaggca gacatctgtg aatcgcttca cgaccacgct   4860
gatgagcttt accgcagctg cctcgcgcgt ttcggtgatg acggtgaaaa cctctgacac   4920
atgcagctcc cggagacggt cacagcttgt ctgtaagcgg atgccgggag cagacaagcc   4980
cgtcagggcg cgtcagcggg tgttggcggg tgtcggggcg cagccatgac ccagtcacgt   5040
agcgatagcg gagtgtatac tggcttaact atgcggcatc agagcagatt gtactgagag   5100
tgcaccatat atgcggtgtg aaataccgca cagatgcgta aggagaaaat accgcatcag   5160
gcgctcttcc gcttcctcgc tcactgactc gctgcgctcg gtcgttcggc tgcggcgagc   5220
ggtatcagct cactcaaagg cggtaatacg gttatccaca gaatcagggg ataacgcagg   5280
aaagaacatg tgagcaaaag gccagcaaaa ggccaggaac cgtaaaaagg ccgcgttgct   5340
ggcgtttttc cataggctcc gcccccctga cgagcatcac aaaaatcgac gctcaagtca   5400
gaggtggcga aacccgacag gactataaag ataccaggcg tttccccctg gaagctccct   5460
cgtgcgctct cctgttccga ccctgccgct taccggatac ctgtccgcct ttctcccttc   5520
gggaagcgtg gcgctttctc atagctcacg ctgtaggtat ctcagttcgg tgtaggtcgt   5580
tcgctccaag ctgggctgtg tgcacgaacc ccccgttcag cccgaccgct gcgccttatc   5640
cggtaactat cgtcttgagt ccaacccggt aagacacgac ttatcgccac tggcagcagc   5700
cactggtaac aggattagca gagcgaggta tgtaggcggt gctacagagt tcttgaagtg   5760
gtggcctaac tacggctaca ctagaaggac agtatttggt atctgcgctc tgctgaagcc   5820
agttaccttc ggaaaaagag ttggtagctc ttgatccggc aaacaaacca ccgctggtag   5880
cggtggtttt tttgtttgca agcagcagat tacgcgcaga aaaaaaggat ctcaagaaga   5940
tcctttgatc ttttctacgg ggtctgacgc tcagtggaac gaaaactcac gttaagggat   6000
tttggtcatg aacaataaaa ctgtctgctt acataaacag taatacaagg ggtgttatga   6060
gccatattca acgggaaacg tcttgctcta ggccgcgatt aaattccaac atggatgctg   6120
atttatatgg gtataaatgg gctcgcgata atgtcgggca atcaggtgcg acaatctatc   6180
gattgtatgg gaagcccgat gcgccagagt tgtttctgaa acatggcaaa ggtagcgttg   6240
ccaatgatgt tacagatgag atggtcagac taaactggct gacggaattt atgcctcttc   6300
cgaccatcaa gcattttatc cgtactcctg atgatgcatg gttactcacc actgcgatcc   6360
ccgggaaaac agcattccag gtattagaag aatatcctga ttcaggtgaa aatattgttg   6420
atgcgctggc agtgttcctg cgccggttgc attcgattcc tgtttgtaat tgtcctttta   6480
acagcgatcg cgtatttcgt ctcgctcagg cgcaatcacg aatgaataac ggtttggttg   6540
atgcgagtga ttttgatgac gagcgtaatg gctggcctgt tgaacaagtc tggaaagaaa   6600
tgcataaact tttgccattc tcaccggatt cagtcgtcac tcatggtgat ttctcacttg   6660
ataaccttat ttttgacgag gggaaattaa taggttgtat tgatgttgga cgagtcggaa   6720
tcgcagaccg ataccaggat cttgccatcc tatggaactg cctcggtgag ttttctcctt   6780
cattacagaa acggcttttt caaaaatatg gtattgataa tcctgatatg aataaattgc   6840
agtttcattt gatgctcgat gagtttttct aagaattaat tcatgagcgg atacatattt   6900
gaatgtattt agaaaaataa acaaataggg gttccgcgca catttccccg aaaagtgcca   6960
cctgaaattg taaacgttaa tattttgtta aaattcgcgt taaatttttg ttaaatcagc   7020
```

```
tcatttttta accaataggc cgaaatcggc aaaatccctt ataaatcaaa agaatagacc   7080

gagatagggt tgagtgttgt tccagtttgg aacaagagtc cactattaaa gaacgtggac   7140

tccaacgtca aagggcgaaa aaccgtctat cagggcgatg gcccactacg tgaaccatca   7200

ccctaatcaa gtttttttggg gtcgaggtgc cgtaaagcac taaatcggaa ccctaaaggg   7260

agcccccgat ttagagcttg acggggaaag ccggcgaacg tggcgagaaa ggaagggaag   7320

aaagcgaaag gagcgggcgc tagggcgctg gcaagtgtag cggtcacgct gcgcgtaacc   7380

accacacccg ccgcgcttaa tgcgccgcta cagggcgcgt cccattcgcc a            7431


<210> SEQ ID NO 10
<211> LENGTH: 37
<212> TYPE: DNA
<213> ORGANISM: Artificial Sequence
<220> FEATURE:
<223> OTHER INFORMATION: primer

<400> SEQUENCE: 10

gatataggat cctcatttgt agcttgtgga acaacag                              37


<210> SEQ ID NO 11
<211> LENGTH: 42
<212> TYPE: DNA
<213> ORGANISM: Artificial Sequence
<220> FEATURE:
<223> OTHER INFORMATION: primer

<400> SEQUENCE: 11

caatatgtcg acttgtgtta caccattagt tggtactgta cc                        42


<210> SEQ ID NO 12
<211> LENGTH: 40
<212> TYPE: DNA
<213> ORGANISM: Artificial Sequence
<220> FEATURE:
<223> OTHER INFORMATION: primer

<400> SEQUENCE: 12

gatccagata atccaagatg gattaatgca caaaaagata                          40


<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13

tatcttttttg tgcattaatc catcttggat tatctggatc                          40


<210> SEQ ID NO 14
<211> LENGTH: 40
<212> TYPE: DNA
<213> ORGANISM: Artificial Sequence
<220> FEATURE:
<223> OTHER INFORMATION: primer

<400> SEQUENCE: 14

caaaatgcac aaaacaactg gttaactcaa caagcaaact                          40


<210> SEQ ID NO 15
<211> LENGTH: 40
<212> TYPE: DNA
<213> ORGANISM: Artificial Sequence
```

<220> FEATURE:
<223> OTHER INFORMATION: primer

<400> SEQUENCE: 15
agtttgcttg ttgagttaac cagttgtttt gtgcattttg 40

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16
ggttcaactt catatgattg gtatgtttct tacgataatg 40

<210> SEQ ID NO 17
<211> LENGTH: 40
<212> TYPE: DNA
<213> ORGANISM: Artificial Sequence
<220> FEATURE:
<223> OTHER INFORMATION: primer

<400> SEQUENCE: 17
cattatcgta agaaacatac caatcatatg aagttgaacc 40

<210> SEQ ID NO 18
<211> LENGTH: 32
<212> TYPE: DNA
<213> ORGANISM: Artificial Sequence
<220> FEATURE:
<223> OTHER INFORMATION: primer

<400> SEQUENCE: 18
ttatgttcca ggatggaatt acggagacgc tg 32

<210> SEQ ID NO 19
<211> LENGTH: 32
<212> TYPE: DNA
<213> ORGANISM: Artificial Sequence
<220> FEATURE:
<223> OTHER INFORMATION: primer

<400> SEQUENCE: 19
cagcgtctcc gtaattccat cctggaacat aa 32

<210> SEQ ID NO 20
<211> LENGTH: 46
<212> TYPE: DNA
<213> ORGANISM: Artificial Sequence
<220> FEATURE:
<223> OTHER INFORMATION: primer

<400> SEQUENCE: 20
gatataggat ccatggcaaa agaaattatt ttaggaatag atttag 46

<210> SEQ ID NO 21
<211> LENGTH: 45
<212> TYPE: DNA
<213> ORGANISM: Artificial Sequence
<220> FEATURE:
<223> OTHER INFORMATION: primer

<400> SEQUENCE: 21
caatatgtcg acttaatttt ctttaacttc agcttcaatt ggttg 45

<210> SEQ ID NO 22
<211> LENGTH: 58
<212> TYPE: DNA
<213> ORGANISM: Artificial Sequence
<220> FEATURE:
<223> OTHER INFORMATION: primer

<400> SEQUENCE: 22
gatgactgtg atcatgttat tgttgattgg ttagttgaca aaattaaaaa agaatatg 58

<210> SEQ ID NO 23
<211> LENGTH: 58
<212> TYPE: DNA
<213> ORGANISM: Artificial Sequence
<220> FEATURE:
<223> OTHER INFORMATION: primer

<400> SEQUENCE: 23
catattcttt tttaattttg tcaactaacc aatcaacaat aacatgatca cagtcatc 58

<210> SEQ ID NO 24
<211> LENGTH: 43
<212> TYPE: DNA
<213> ORGANISM: Artificial Sequence
<220> FEATURE:
<223> OTHER INFORMATION: primer

<400> SEQUENCE: 24
caatatggat cctcttgtgg acaaccaacc acaattaaat ttg 43

<210> SEQ ID NO 25
<211> LENGTH: 60
<212> TYPE: DNA
<213> ORGANISM: Artificial Sequence
<220> FEATURE:
<223> OTHER INFORMATION: primer

<400> SEQUENCE: 25
gtataagtcg acttagtgat ggtgatggtg atgagctgca gatttttcgg ccataaaatc 60

<210> SEQ ID NO 26
<211> LENGTH: 38
<212> TYPE: DNA
<213> ORGANISM: Artificial Sequence
<220> FEATURE:
<223> OTHER INFORMATION: primer

<400> SEQUENCE: 26
cttctcaagg ttcatattgg ccaatgatgc taggaatg 38

<210> SEQ ID NO 27
<211> LENGTH: 38
<212> TYPE: DNA
<213> ORGANISM: Artificial Sequence
<220> FEATURE:
<223> OTHER INFORMATION: primer

<400> SEQUENCE: 27
cattcctagc atcattggcc aatatgaacc ttgagaag 38

<210> SEQ ID NO 28
<211> LENGTH: 40
<212> TYPE: DNA
<213> ORGANISM: Artificial Sequence
<220> FEATURE:
<223> OTHER INFORMATION: primer

<400> SEQUENCE: 28
actaagcaaa gctctgattg gaatcttatt ttaggaaaca 40

<210> SEQ ID NO 29
<211> LENGTH: 40
<212> TYPE: DNA
<213> ORGANISM: Artificial Sequence
<220> FEATURE:
<223> OTHER INFORMATION: primer

<400> SEQUENCE: 29
tgtttcctaa aataagattc caatcagagc tttgcttagt 40

<210> SEQ ID NO 30
<211> LENGTH: 53
<212> TYPE: DNA
<213> ORGANISM: Artificial Sequence
<220> FEATURE:
<223> OTHER INFORMATION: primer

<400> SEQUENCE: 30
ctttctaaaa ctaataaaac tttttggagt gaaaaaagtt tacaaaataa caa 53

<210> SEQ ID NO 31
<211> LENGTH: 53
<212> TYPE: DNA
<213> ORGANISM: Artificial Sequence
<220> FEATURE:
<223> OTHER INFORMATION: primer

<400> SEQUENCE: 31
ttgttatttt gtaaactttt ttcactccaa aaagttttat tagttttaga aag 53

<210> SEQ ID NO 32
<211> LENGTH: 46
<212> TYPE: DNA
<213> ORGANISM: Artificial Sequence
<220> FEATURE:
<223> OTHER INFORMATION: primer

<400> SEQUENCE: 32
gttgaaaacc aatatcaaga atgggaaaac actttaaaac aaacac 46

<210> SEQ ID NO 33
<211> LENGTH: 46
<212> TYPE: DNA
<213> ORGANISM: Artificial Sequence
<220> FEATURE:
<223> OTHER INFORMATION: primer

<400> SEQUENCE: 33
gtgtttgttt taaagtgttt tcccattctt gatattggtt ttcaac 46

<210> SEQ ID NO 34
<211> LENGTH: 53
<212> TYPE: DNA
<213> ORGANISM: Artificial Sequence
<220> FEATURE:
<223> OTHER INFORMATION: primer

<400> SEQUENCE: 34
caagcaaata ctgaaactac ttcatggaca aaaaaagata ttcaaactaa atc 53

<210> SEQ ID NO 35

<211> LENGTH: 53
<212> TYPE: DNA
<213> ORGANISM: Artificial Sequence
<220> FEATURE:
<223> OTHER INFORMATION: primer

<400> SEQUENCE: 35
gatttagttt gaatatcttt ttttgtccat gaagtagttt cagtatttgc ttg 53

<210> SEQ ID NO 36
<211> LENGTH: 58
<212> TYPE: DNA
<213> ORGANISM: Artificial Sequence
<220> FEATURE:
<223> OTHER INFORMATION: primer

<400> SEQUENCE: 36
ctgaatactt taaacctata aatcaatggg gatcttttga aattagacaa tatttaac 58

<210> SEQ ID NO 37
<211> LENGTH: 58
<212> TYPE: DNA
<213> ORGANISM: Artificial Sequence
<220> FEATURE:
<223> OTHER INFORMATION: primer

<400> SEQUENCE: 37
gttaaatatt gtctaatttc aaaagatccc cattgattta taggtttaaa gtattcag 58

<210> SEQ ID NO 38
<211> LENGTH: 44
<212> TYPE: DNA
<213> ORGANISM: Artificial Sequence
<220> FEATURE:
<223> OTHER INFORMATION: primer

<400> SEQUENCE: 38
ctattctgta gattctcctt ggtcacgtgc attttttaaa aaag 44

<210> SEQ ID NO 39
<211> LENGTH: 44
<212> TYPE: DNA
<213> ORGANISM: Artificial Sequence
<220> FEATURE:
<223> OTHER INFORMATION: primer

<400> SEQUENCE: 39
cttttttaaa aaatgcacgt gaccaaggag aatctacaga atag 44

<210> SEQ ID NO 40
<211> LENGTH: 45
<212> TYPE: DNA
<213> ORGANISM: Artificial Sequence
<220> FEATURE:
<223> OTHER INFORMATION: primer

<400> SEQUENCE: 40
gaaaacaaaa agcttcagaa tggacaacaa gagaagatgt ttatg 45

<210> SEQ ID NO 41
<211> LENGTH: 45
<212> TYPE: DNA
<213> ORGANISM: Artificial Sequence
<220> FEATURE:
<223> OTHER INFORMATION: primer -continued

<400> SEQUENCE: 41

```
cataaacatc ttctcttgtt gtccattctg aagctttttg ttttc                 45
```